US010451548B2

(12) United States Patent
Gemp et al.

(10) Patent No.: US 10,451,548 B2
(45) Date of Patent: Oct. 22, 2019

(54) ACTIVE HYPERSPECTRAL IMAGING SYSTEM

(71) Applicant: The MITRE Corporation, McLean, VA (US)

(72) Inventors: Kevin Gemp, Falls Church, VA (US); Ariel Schlamm, Washington, DC (US); Christopher Miller, Darnestown, MD (US); Shannon Jordan, Fairfax, VA (US); Marin Halper, Washington, DC (US); Brent Bartlett, Falls Church, VA (US)

(73) Assignee: The MITRE Corporation, McLean, VA (US)

( * ) Notice: Subject to any disclaimer, the term of this patent is extended or adjusted under 35 U.S.C. 154(b) by 219 days.

(21) Appl. No.: 14/997,300

(22) Filed: Jan. 15, 2016

(65) Prior Publication Data

US 2017/0205344 A1    Jul. 20, 2017

(51) Int. Cl.
  *G01N 21/55*    (2014.01)
  *G01N 21/27*    (2006.01)

(52) U.S. Cl.
  CPC ............ *G01N 21/55* (2013.01); *G01N 21/27* (2013.01); *G01N 2201/0612* (2013.01); *G01N 2201/0621* (2013.01)

(58) Field of Classification Search
  CPC ................. G01N 21/55; G01N 21/27; G01N 2201/0621; G01N 2201/0612;
  (Continued)

(56) References Cited

U.S. PATENT DOCUMENTS

| 4,030,837 A | * | 6/1977 | Kojima | ................ G01N 21/55 356/30 |
| 5,144,498 A | * | 9/1992 | Vincent | ................... G01J 3/12 250/226 |

(Continued)

FOREIGN PATENT DOCUMENTS

| WO | WO 2010/082852 | 7/2010 |
| WO | WO 2014/143276 | 9/2014 |
| WO | WO 2014/143338 | 9/2014 |

OTHER PUBLICATIONS

VeroVision "Portable Standoff Detection for Real-time Safety"; Apr. 2014; located at http://marketing.chemimage.com/acton/attachment/1703/f-0106/1/-/-/-/-/VeroVision-Product-Sheet4-bluer.pdf—2 pages.

(Continued)

*Primary Examiner* — Mohamed K Amara
(74) *Attorney, Agent, or Firm* — Morrison & Foerster LLP

(57) ABSTRACT

A system for generating reflectance values for a target that includes a plurality of electromagnetic radiation sources for irradiating the target, an imager for generating a plurality of digital representations of the target that includes an array of filter elements for filtering electromagnetic radiation reflected by the target through an array of filter elements, and a detector for detecting the filtered electromagnetic radiation at an array of detection elements. The system includes processors for determining a set of reflectance values for a portion of the target based on a first digital representation of the target generated in response to irradiation of the target with radiation of a first wavelength band and a second digital representation of the target generated in response to irradiation of the target with radiation of a second wavelength band.

36 Claims, 9 Drawing Sheets

(58) Field of Classification Search
CPC ............ G01N 21/59; G01N 2201/062; G01N 21/9501; G01N 21/4738; G01N 21/255; G01N 21/21; G01N 21/274; G01N 21/31; G01N 21/8422; G01N 21/359; G01N 21/474; G01N 21/47; G01N 21/39; G01N 2021/556; G01N 2201/08; G01N 2201/06113; G01N 21/8806
See application file for complete search history.

(56) References Cited

U.S. PATENT DOCUMENTS

| | | | | |
|---|---|---|---|---|
| 5,784,507 | A * | 7/1998 | Holm-Kennedy | G01J 3/0259 250/227.23 |
| 6,573,490 | B2 | 6/2003 | Hochstein | |
| 7,369,229 | B2 | 5/2008 | Bissett, III et al. | |
| 7,426,040 | B2 * | 9/2008 | Kim | B82Y 20/00 356/519 |
| 7,433,042 | B1 | 10/2008 | Cavanaugh et al. | |
| 8,139,213 | B2 * | 3/2012 | Bahatt | G01N 21/0332 356/328 |
| 8,249,308 | B2 | 8/2012 | Lussier | |
| 8,395,770 | B1 * | 3/2013 | Hug | G01J 3/10 356/317 |
| 9,103,714 | B2 | 8/2015 | Treado et al. | |
| 2002/0135768 | A1 * | 9/2002 | Sugiyama | G01N 21/27 356/405 |
| 2005/0174584 | A1 * | 8/2005 | Chalmers | G01B 11/0625 356/630 |
| 2005/0213089 | A1 | 9/2005 | Margalith et al. | |
| 2006/0054782 | A1 * | 3/2006 | Olsen | H04N 5/265 250/208.1 |
| 2006/0065989 | A1 * | 3/2006 | Druffel | B29C 35/0805 264/1.32 |
| 2007/0159541 | A1 | 7/2007 | Sparks et al. | |
| 2008/0285026 | A1 * | 11/2008 | Okawauchi | G01M 11/005 356/300 |
| 2009/0245605 | A1 * | 10/2009 | Levenson | A61B 5/0059 382/128 |
| 2010/0013979 | A1 | 1/2010 | Golub et al. | |
| 2010/0210951 | A1 | 8/2010 | Rahman et al. | |
| 2011/0019190 | A1 * | 1/2011 | Sakai | G01N 21/3563 356/365 |
| 2011/0261351 | A1 | 10/2011 | Treado et al. | |
| 2012/0062740 | A1 | 3/2012 | Treado et al. | |
| 2012/0170024 | A1 | 7/2012 | Azzazy et al. | |
| 2013/0004065 | A1 | 1/2013 | Ma | |
| 2013/0122607 | A1 * | 5/2013 | Kashiwazaki | G01N 21/77 436/501 |
| 2014/0085629 | A1 | 3/2014 | Bodkin et al. | |
| 2015/0015692 | A1 * | 1/2015 | Smart | G01J 3/2823 348/77 |
| 2015/0185081 | A1 | 7/2015 | Sano et al. | |
| 2015/0214425 | A1 * | 7/2015 | Taylor | H01S 5/0421 385/14 |
| 2016/0040985 | A1 * | 2/2016 | Nagai | G01J 3/14 356/328 |
| 2016/0139296 | A1 * | 5/2016 | Perkins | E21B 47/102 356/416 |
| 2016/0238447 | A1 * | 8/2016 | Cho | G01J 3/0224 |
| 2017/0234675 | A1 * | 8/2017 | Iddan | G01B 9/02004 356/479 |

OTHER PUBLICATIONS

American Infrared Solutions Application Note "Short Wave Infrared (SWIR) Imaging for Hyperspectral and Surveillance Systems"; Jun. 2014; located at http://www.go-airs.com/wp-content/uploads/2014/06/SWIR-Application-Note-AIRS-0614.pdf—3 pages.
BaySpec SuperGamut™ "SWIR Imaging Spectrometer"; 2015; located at http://www.bayspec.com/news/bayspecs-new-supergamut-swir-imaging-spectrographs/—2 pages.
American Infrared Solutions "mini-Nyx-S 640"; Mar. 2015; located at http://www.go-airs.com/wp-content/uploads/2015/04/mini-Nyx-S-640-SWIR-0415.pdf—2 pages.
Headwall Hyperspec® "SWIR Imaging Sensor for the 900nm to 2500 nm spectral range"; 2014; located at http://cdn2.hubspot.net/hubfs/145999/docs/SWIR.pdf?t=1444235571262—2 pages.
Night Vision Systems "(SWIR) Short Wave Infrared Night Vision Camera Systems for Vehicle Navigation"; Oct. 2015; located at http://www.sensorsinc.com/applications/military/night-vision-systems/—4 pages.
Sensors Unlimited "Why SWIR? What Is the Value of Shortwave Infrared?"; Oct. 2015; located at www.sensorsinc.com/technology/why-swir/—4 pages.
BaySpec "BaySpec's New SuperCamut™ SWIR Imaging Spectrographs"; Oct. 2015; located at http://2k2n5lweb121vmcuk3gwalro.wpengine.netdna-cdn.com/wp-content/uploads/2015/08/BaySpec-Datasheet-NIRS-0900-1700m-with-lens1.pdf—1 page.
BaySpec "SuperGamut™ SWIR Imaging Spectrographs"; Oct. 2015; located at http://www.bayspec.com/uncategorized/supergamut-swir-imaging-spectrographs/—2 pages.
Park, Jong-Il et al., 2007, "Multispectral Imaging Using Multiplexed Illumination," IEEE International Conference on Computer Vision; 8 pages.
Dame, A., 2010, "A Unified Direct Approach for Visual Servoing and Visual Tracking Using Mutual Information," Diss. Universite Rennes 1; 180 pages.
Xu, L. et al., 2010, "Two-Phase Kernel Estimation for Robust Motion Deblurring," Department of Computer Science and Engineering, The Chinese University of Hong Kong; 14 pages.
Dame, A. et al., 2012, "Second Order Optimization of Mutual Information for Real-Time Image Registration," IEEE Trans on Image Processing 21.9; 14 pages.
Henrot, S. et al., 2013, "Fast positive deconvolution of hyperspectral images," IEEE Trans on Image Processing 22.2; 7 pages.

* cited by examiner

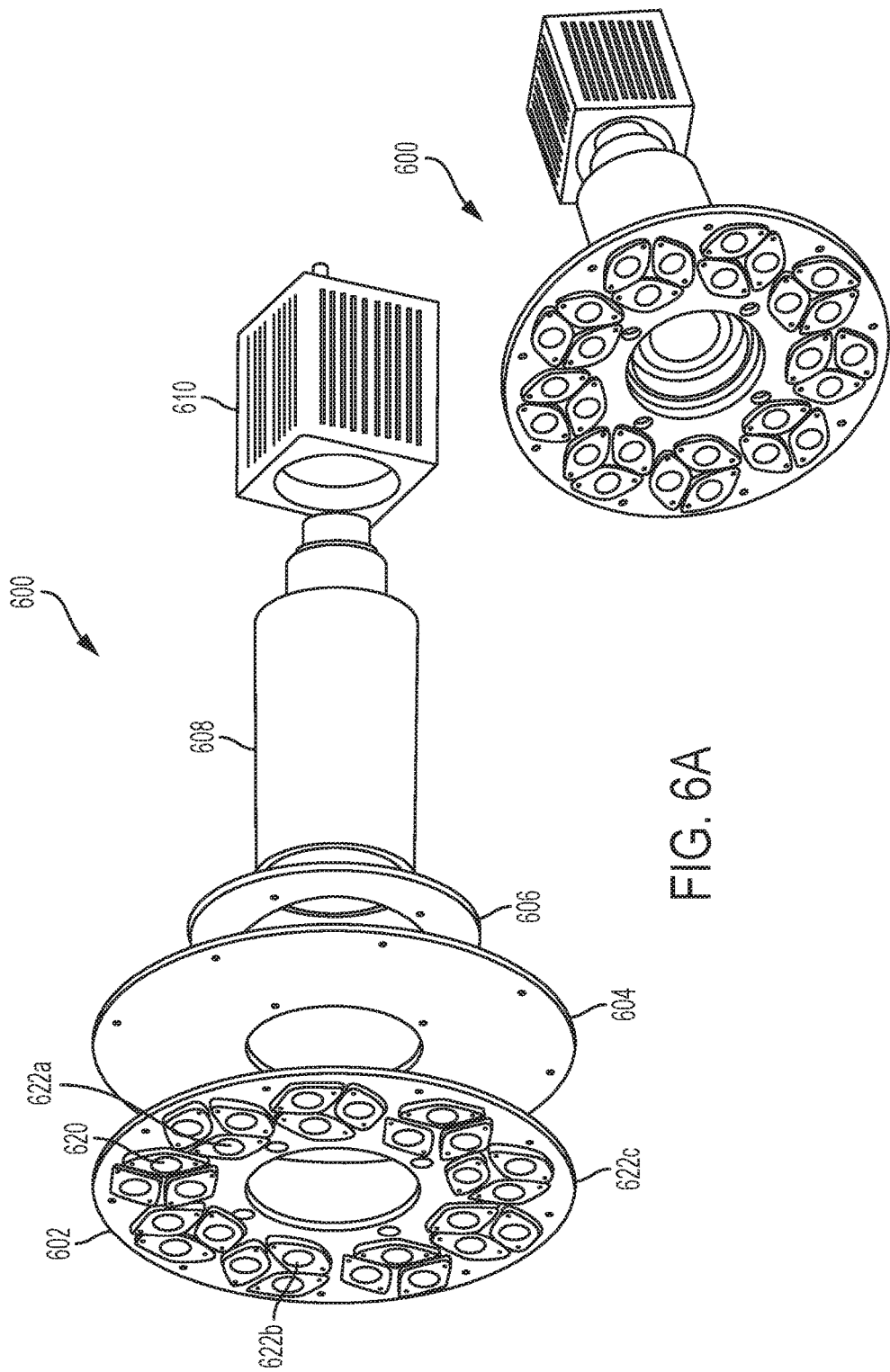

ACTIVE HYPERSPECTRAL IMAGING SYSTEM

STATEMENT REGARDING FEDERALLY SPONSORED RESEARCH OR DEVELOPMENT

This invention was made with Government support under U.S. Government contract W56KGU-14-C-0010 awarded by the U.S. Department of the Army. The Government has certain rights in this invention.

FIELD OF THE INVENTION

The invention relates generally to spectrometry and particularly to hyperspectral imaging.

BACKGROUND OF THE INVENTION

Spectral imagers measure the reflectance energy spectrum of materials within a field of view. The reflectance, reflectivity, or reflectance coefficient is a number between 0 and 1 that determines the proportion of light at a given wavelength that is reflected by a particular material (as opposed to being absorbed). Leaves, for example, reflect photons in the green portion of the visible spectrum at a much greater proportion than photons in the red or blue portion. The reflectance spectrum of a material contains the reflectance coefficient for that material at each wavelength within a relevant range. The reflectance spectrum is valuable because it contains information about a material's chemical makeup and constituents. This type of information is useful in several domains, including, but not limited to, agriculture, geology, astronomy, defense, and intelligence applications.

Spectral imagers record energy from the field of view at a multitude of spatial picture elements (pixels). The recorded energy is radiance, which contains the material reflectance information as well as other sources of information, including illumination conditions and atmospheric conditions. The raw collected imagery can be converted to reflectance values at each of multiple spectral bands per pixel. The data set generated by spectral imagers is a three-dimensional "cube" having two spatial dimensions and one spectral dimension.

Hyperspectral imagers are a class of spectral imagers that can generate a spectral cube with relatively higher resolution in the spectral dimension. Hyperspectral imaging is typically defined by having tens to hundreds of discrete spectral bands within a certain wavelength region. Conventional hyperspectral imagers may rely on either sequentially capturing a series of spatial images, each spatial image representing a certain spectral component ("pushbroom imagers"), or sequentially capturing a series of spectral profiles, each spectral profile representing a certain spatial portion ("staring imagers"). Generally, in both pushbroom and staring imagers, one or more components, such as an aperture, mirror, or filter, is physically moved to perform a scan over either the spectral or spatial dimensions. Precise control of the movement of these components is important to generation of high spatial and spectral resolution.

Conventional hyperspectral imagers are large and complex devices that are unsuitable for hand-held or portable applications and are too costly for many applications.

BRIEF SUMMARY OF THE INVENTION

A hyperspectral imaging system for measuring a reflectance spectrum of a scene using multiple active electromagnetic radiation sources in conjunction with a multispectral imager. According to some embodiments, the system can provide portable and affordable hyperspectral imaging with reduced size, weight, power, and cost. The system can capture multiple multispectral frames of a target scene over a period of time while varying the wavelengths of the electromagnetic radiation irradiating the target scene by sequentially activating the radiation sources. The information in the frames can be used in conjunction with the known spectral characteristics of the radiation sources and multispectral imager to determine the hyperspectral reflectance spectrum of the target scene.

The multispectral imager can include an array of filters overlaying an array of detection elements (also referred to herein as pixel elements or pixels) that generate a signal proportional to the amount of incident radiation. The array of filters includes multiple filter types, each having a different spectral response, such that a frame collected based on the signals of the array of detection elements is multispectral.

The active electromagnetic radiation sources may each generate radiation in a different wavelength band. By alternately activating radiation sources while collecting frames, additional spectral information can be obtained. Additional frames may be collected to measure sensor noise and to measure ambient contributions to the radiation detected by the imager. Some or all of these frames may be processed to generate a spectral cube with two spatial dimensions and a reflectance dimension. For a given spatial point (pixel), reflectance values may be determined for each of several narrow spectral bands over a continuous spectral range.

According to some embodiments, a system for generating reflectance values for a target comprises a plurality of electromagnetic radiation sources for irradiating the target, an imager for generating a plurality of digital representations of the target comprising an array of filter elements for filtering electromagnetic radiation reflected by the target through an array of filter elements, and a detector for detecting the filtered electromagnetic radiation at an array of detection elements. The system includes one or more processors for determining a set of reflectance values for a portion of the target based on a first digital representation of the target generated in response to irradiation of the target with radiation of a first wavelength band and a second digital representation of the target generated in response to irradiation of the target with radiation of a second wavelength band, wherein each reflectance value in the set of reflectance values corresponds to the reflectance of the portion of the target at a different wavelength band, and memory for storing the set of reflectance values.

In any of these embodiments, the first wavelength band may overlap the second wavelength band. In any of these embodiments, the first wavelength band may not overlap the second wavelength band. In any of these embodiments, the array of filter elements may comprise filter elements of a first type for passing electromagnetic radiation in a first filtering wavelength band and filter elements of a second type for passing electromagnetic radiation in a second filtering wavelength band.

In any of these embodiments, the filter elements of the first type may be interspersed with the filter elements of the second type. In any of these embodiments, the first filtering wavelength band and the second filtering wavelength band may each be different from the first wavelength band and the second wavelength band.

In any of these embodiments, the first filtering wavelength band may overlap one or more of the second filtering wavelength band, the first wavelength band, and the second wavelength band. In any of these embodiments, each filter element in the array of filter elements may correspond to a detection element in the array of detection elements.

In any of these embodiments, radiation reflected by the target may pass through an aperture prior to reaching the array of filter elements and the aperture is fixed relative to the array of filter elements. In any of these embodiments, the first electromagnetic radiation source may comprise an array of light emitting diodes or an array of laser diodes.

In any of these embodiments, the first digital representation may comprise an array of intensity values, each intensity value corresponding to an intensity of total electromagnetic radiation detected at the respective detection element of the array of detection elements, and the total electromagnetic radiation may include electromagnetic radiation from sources other than the first electromagnetic radiation source.

In any of these embodiments, the filter array may comprise M filter types, the processing unit may be configured to determine a set of M×N reflectance values for a portion of the target based on N digital representation of the target, each digital representation generated based on irradiation of the target by a respective one of N electromagnetic radiation sources, and each reflectance value in the set of reflectance values may correspond to the reflectance of the portion of the target at a discrete wavelength band.

According to some embodiments, a method for generating reflectance values for a target includes irradiating the target with radiation of a first wavelength band, wherein the radiation of the first wavelength band is generated by a first electromagnetic radiation source, filtering the electromagnetic radiation of the first wavelength band reflected by the target through an array of filter elements, detecting the filtered electromagnetic radiation of the first wavelength band reflected by the target at an array of detection elements, generating a first digital representation of the target based on the detected filtered electromagnetic radiation of the first wavelength band reflected by the target, irradiating the target with radiation of a second wavelength band, wherein the radiation of the second wavelength band is generated by a second electromagnetic radiation source, filtering the electromagnetic radiation of the second wavelength band reflected by the target through the array of filter elements, detecting the filtered electromagnetic radiation of the second wavelength band reflected by the target at the array of detection elements, generating a second digital representation of the target based on the detected filtered electromagnetic radiation of the second wavelength band reflected by the target, and determining a set of reflectance values for a portion of the target based on the first digital representation and the second digital representation, wherein each reflectance value in the set of reflectance values corresponds to the reflectance of the portion of the target at a different wavelength band.

In any of these embodiments, the first wavelength band may overlap the second wavelength band. In any of these embodiments, the first wavelength band may not overlap the second wavelength band. In any of these embodiments, the array of filter elements may comprise filter elements of a first type for passing electromagnetic radiation in a first filtering wavelength band and filter elements of a second type for passing electromagnetic radiation in a second filtering wavelength band.

In any of these embodiments, the filter elements of the first type may be interspersed with the filter elements of the second type. In any of these embodiments, the first filtering wavelength band and the second filtering wavelength band may each be different from the first wavelength band and the second wavelength band.

In any of these embodiments, the first filtering wavelength band may overlap one or more of the second filtering wavelength band, the first wavelength band, and the second wavelength band. In any of these embodiments, each filter element in the array of filter elements may correspond to a detection element in the array of detection elements.

In any of these embodiments, radiation reflected by the target may pass through an aperture prior to reaching the array of filter elements and the aperture is fixed relative to the array of filter elements. In any of these embodiments, the first electromagnetic radiation source may comprise an array of light emitting diodes or an array of laser diodes.

In any of these embodiments, the first digital representation may comprise an array of intensity values, each intensity value corresponding to an intensity of total electromagnetic radiation detected at the respective detection element of the array of detection elements, and the total electromagnetic radiation may include electromagnetic radiation from sources other than the first electromagnetic radiation source.

In any of these embodiments, the filter array may comprise M filter types, and the method may include generating N digital representation of the target, each digital representation generated based on irradiation of the target by a respective one of N electromagnetic radiation sources, and determining a set of M×N reflectance values for a portion of the target based on the N digital images, wherein each reflectance value in the set of reflectance values corresponds to the reflectance of the portion of the target at a discrete wavelength band.

According to some embodiments, a handheld electronic device for collecting digital representations of a target includes a plurality of electromagnetic radiation sources for irradiating the target, an imager for generating a plurality of digital representations of the target, the imager comprising an array of filter elements for filtering electromagnetic radiation reflected by the target through an array of filter elements, and a detector for detecting the filtered electromagnetic radiation at an array of detection elements. The device includes one or more processors, memory, and one or more programs, wherein the one or more programs are stored in the memory and configured to be executed by the one or more processors, the one or more programs including instructions for activating a first electromagnetic radiation source of the plurality of electromagnetic radiation sources to irradiate the target with radiation of a first wavelength band generated by the first electromagnetic radiation source, triggering the imager to collect a first digital representation of the target, wherein the first digital representation of the target is based on the radiation of the first wavelength band that is reflected by the target and filtered through the array of filter elements, activating a second electromagnetic radiation source of the plurality of electromagnetic radiation sources to irradiate the target with radiation of a second wavelength band generated by the second electromagnetic radiation source, and triggering the imager to collect a second digital representation of the target, wherein the second digital representation of the target is based on the radiation of the second wavelength band that is reflected by the target and filtered through the array of filter elements.

In any of these embodiments, the first wavelength band may overlap the second wavelength band. In any of these embodiments, the first wavelength band may not overlap the second wavelength band. In any of these embodiments, the array of filter elements may comprise filter elements of a first type for passing electromagnetic radiation in a first filtering wavelength band and filter elements of a second type for passing electromagnetic radiation in a second filtering wavelength band.

In any of these embodiments, the filter elements of the first type may be interspersed with the filter elements of the second type. In any of these embodiments, the first filtering wavelength band and the second filtering wavelength band may each be different from the first wavelength band and the second wavelength band.

In any of these embodiments, the first filtering wavelength band may overlap one or more of the second filtering wavelength band, the first wavelength band, and the second wavelength band. In any of these embodiments, each filter element in the array of filter elements may correspond to a detection element in the array of detection elements.

In any of these embodiments, radiation reflected by the target may pass through an aperture prior to reaching the array of filter elements and the aperture is fixed relative to the array of filter elements. In any of these embodiments, the first electromagnetic radiation source may comprise an array of light emitting diodes or an array of laser diodes.

In any of these embodiments, the first digital representation may comprise an array of intensity values, each intensity value corresponding to an intensity of total electromagnetic radiation detected at the respective detection element of the array of detection elements, and the total electromagnetic radiation may include electromagnetic radiation from sources other than the first electromagnetic radiation source.

In any of these embodiments, the filter array may comprise M filter types, and the one or more programs may include instructions for generating N digital representation of the target, each digital representation generated based on irradiation of the target by a respective one of N electromagnetic radiation sources, and determining a set of M×N reflectance values for a portion of the target based on the N digital images, wherein each reflectance value in the set of reflectance values corresponds to the reflectance of the portion of the target at a discrete wavelength band.

BRIEF DESCRIPTION OF THE DRAWINGS

FIG. 6A is an exploded view of a hyperspectral imaging device, according to one embodiment;

FIG. 6B is an assembled view of the hyperspectral imaging device of FIG. 6A;

DETAILED DESCRIPTION OF THE INVENTION

Figure 1:
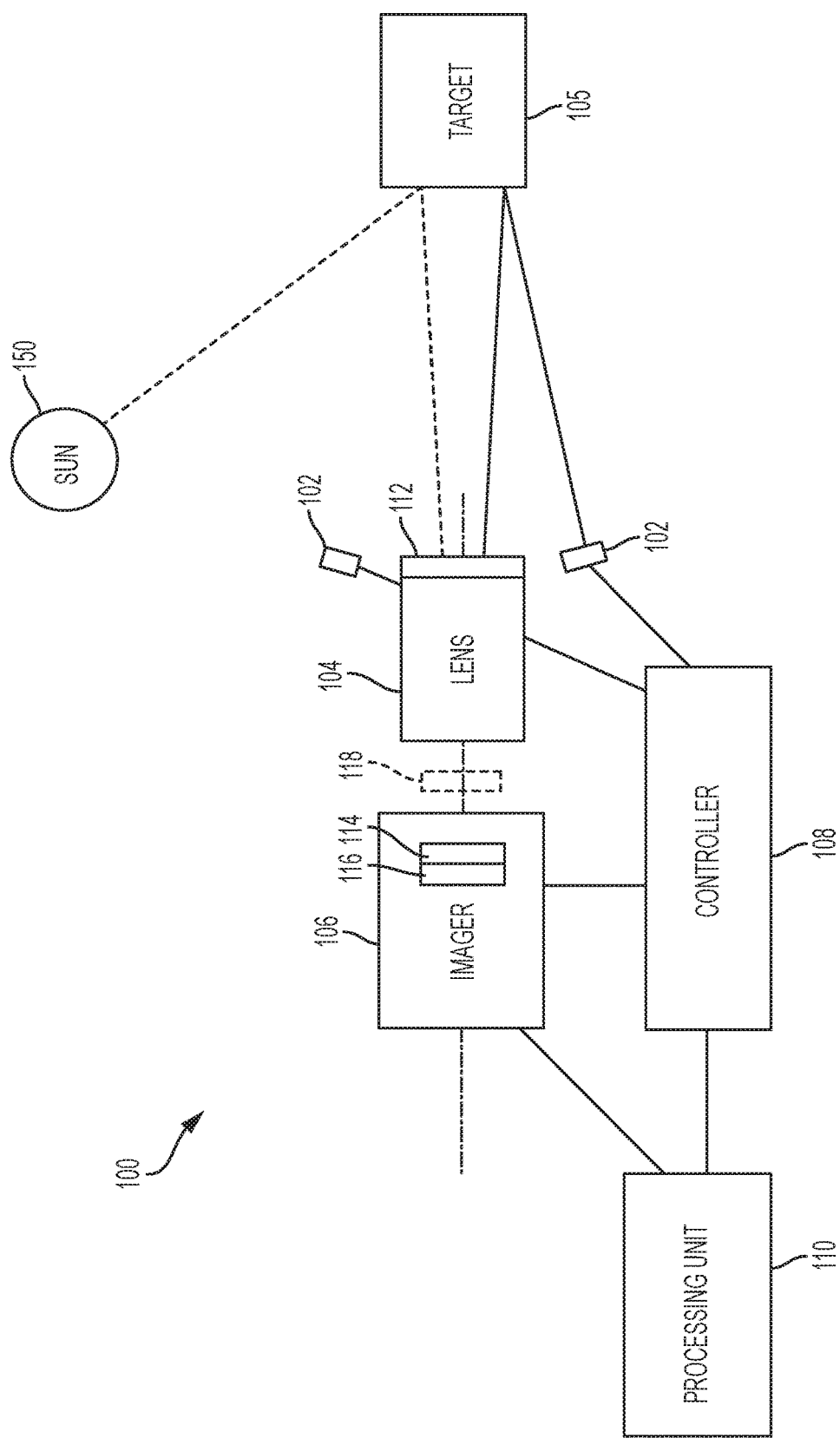
FIG. 1 is a block diagram of a system, according to some embodiments.

Described herein are systems and methods for determining the reflectance spectrum of a target scene using multiple active electromagnetic radiation sources in conjunction with a multispectral imager. The systems and methods collect multiple digital representations (frames) of the target scene based on the electromagnetic radiation reflected by the target scene while alternately activating the electromagnetic radiation sources. The information in the collected frames is then used in conjunction with the known spectral characteristics of the radiation sources and multispectral imager to determine the radiance spectrum of the target. Systems and methods according to some embodiments can be used for hyperspectral imaging of a target scene.

The imager can include an array of detection elements that each generates a signal proportional to the amount of incident radiation in the range of wavelengths to which the element is sensitive. The detection elements may be overlaid by an array of filter elements of different types. The filter types may filter radiation in different wavelength bands, and thus, the radiation detected by the imager can be multispectral. In some embodiments, each radiation source generates radiation in a discrete wavelength band. A frame is captured while the target is illuminated by one of the radiation sources and a subsequent frame is captured while the target is illuminated by a different one of the radiation sources. Frames may be collected in this way for each radiation source. Frames may be collected to measure sensor noise and to measure ambient radiation contributions to the radiation detected by the detector. Some or all of these frames may be processed to generate a spectral cube with two spatial dimensions and a reflectance dimension. For a given spatial point, reflectance values may be determined for each of several spectral bands over a continuous spectral range.

As described in more detail below, the systems and methods according to the present disclosure use active spectral illumination and passive detector (focal plane) filters to reconstruct a higher spectral resolution data cube from multiple lower spectral resolution frames. This approach can reduce the size, weight, power, and cost of an imaging system compared to traditional HSI systems. Embodiments according to the present disclosure can provide data equivalent in spectral resolution to complex, large and expensive HSI systems in a low-cost and handheld form factor. Further, the systems and methods described herein provided an integrated solution leveraging this hardware approach to address the issues of source separation and automatic reflectance conversion for HSI.

In order to effectively exploit HSI, the various electromagnetic radiation sources that are present in a scene must be understood and accounted for. For ground-based collections, the radiation field is a complex mixture of direct and scattered solar radiance. According to some embodiments, the system captures two images per spectral band (per active electromagnetic radiation source of the system), one with the active electromagnetic radiation source turned on and one with the active electromagnetic radiation source turned off. This allows for the removal of contributions from illumination sources (as well as sensor noise artifacts) other than the activated radiation source.

The below description often makes reference to spectroscopy in the visible, near infrared (NIR), and short wave infrared (SWIR) regions of the electromagnetic spectrum, ranging from ~400 nm to ~3000 nm. However, the principles underlying the systems and methods described below are broadly applicable across the electromagnetic spectrum. A person of ordinary skill in the art will appreciate that a given system can be designed to operate in a desired region of the electromagnetic spectrum by selecting or designing appropriate radiation sources, filters, and detectors based on the principles described herein. Further, in the following description, terms such as "image," "illumination," "light," and other similar terms that generally connote electromagnetic radiation in the visible spectrum are often used but are not intended to be limiting to the visible spectrum. It should be understood that, where used, the underlying principles, methods, or devices being described can also be extended, configured, modified, or designed to operate in other regions of the electromagnetic spectrum.

Reference may be made below to "each detection element" in an array of detection elements. In any production detector, some (of the millions of) detector elements (pixels) may be defective or masked intentionally, or some pixel rows, columns, diagonals, or other patterns of pixels may be skipped such that, for example, the pixels either do not generate a signal, generate an insufficient signal, or are not sampled at all. The systems and method according to the present disclosure do not rely on each and every pixel of a detector in order to achieve the results described herein. Rather, it should be understood that as used herein, "each detection element" also refers to cases in which less than all pixels are used in which cases "each detection element" means that the procedure or result is the same for each detection element that is active.

In the following description of the disclosure and embodiments, reference is made to the accompanying drawings in which are shown, by way of illustration, specific embodiments that can be practiced. It is to be understood that other embodiments and examples can be practiced, and changes can be made without departing from the scope of the disclosure.

In addition, it is also to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units, but do not preclude the presence or addition of one or more other features, integers, steps, operations, elements, components, units, and/or groups thereof.

Some portions of the detailed description that follow are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic, or optical signals capable of being stored, transferred, combined, compared, and otherwise manipulated. It is convenient at times, principally for reasons of common usage, to refer to these signals as bits, values, elements, symbols, characters, terms, numbers, or the like. Furthermore, it is also convenient at times to refer to certain arrangements of steps requiring physical manipulations of physical quantities as modules or code devices without loss of generality.

However, all of these and similar terms are to be associated with the appropriate physical quantities and are merely convenient labels applied to these quantities. Unless specifically stated otherwise as apparent from the following discussion, it is appreciated that, throughout the description, discussions utilizing terms such as "processing," "computing," "calculating," "determining," "displaying," or the like, refer to the action and processes of a computer system, or similar electronic computing device, that manipulates and transforms data represented as physical (electronic) quantities within the computer system memories or registers or other such information storage, transmission, or display devices.

Certain aspects of the present invention include process steps and instructions described herein in the form of an algorithm. It should be noted that the process steps and instructions of the present invention could be embodied in software, firmware, or hardware, and, when embodied in software, could be downloaded to reside on and be operated from different platforms used by a variety of operating systems.

The present invention also relates to a device for performing the operations herein. This device may be specially constructed for the required purposes, or it may comprise a general-purpose computer selectively activated or reconfigured by a computer program stored in the computer. Such a computer program may be stored in a non-transitory, computer-readable storage medium, such as, but not limited to, any type of disk, including floppy disks, optical disks, CD-ROMs, magnetic-optical disks, read-only memories (ROMs), random access memories (RAMs), EPROMs, EEPROMs, magnetic or optical cards, application-specific integrated circuits (ASICs), or any type of media suitable for storing electronic instructions and each coupled to a computer system bus. Furthermore, the computers referred to in the specification may include a single processor or may be architectures employing multiple processor designs for increased computing capability.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein.

System

Described below are systems for determining the reflectance spectrum of a target scene using multiple active electromagnetic radiation sources in conjunction with a multispectral imager. The systems can collect multiple frames of the target scene based on the electromagnetic radiation reflected by the target scene while alternately activating the electromagnetic radiation sources. The information in the collected frames can then be processed along with the known spectral characteristics of the radiation sources and multispectral imager to determine the reflectance spectrum of the target.

FIG. 1 is a block diagram of imaging system 100 according to one embodiment.

Imaging system 100 can be used to generate the reflectance spectrum of a target with higher spatial and spectral resolution by capturing multiple lower spatial and spectral resolution frames of the target while irradiating the target with electromagnetic radiation in different wavelength bands. Imaging system 100 includes electromagnetic radiation sources 102, lens 104, imager 106, controller 108, and processing unit 110.

Imaging system 100 may be pointed at target 105 to irradiate target 105 with electromagnetic radiation generated by radiation sources 102 and to receive electromagnetic radiation reflected by target 105. Received radiation passes through aperture 112 and is focused by lens 104 onto imager 106. Imager 106 may generate digital representations (frames) of the target based on the received electromagnetic radiation. Processing unit 110 may use these frames, in conjunction with the characteristics of the radiation sources and the characteristics of the imager, to determine multiple reflectances for each spatial point of the target represented in the frames. In some embodiments, lens 104 is adjustable to focus or zoom in on different portions of a scene. In some embodiments, lens 104 is integral to the imager 106. In some embodiments, an imaging system or device includes swappable lenses to accommodate different imager-to-scene ranges.

Imager 106 includes detector 116 and filter 114 for filtering the electromagnetic radiation before it reaches detector 116. Detector 116 includes an array of detection elements that are configured to generate a signal proportional to the intensity of electromagnetic radiation detected by the element. The signal generated by a detection element can include information about the reflectance of the corresponding portion of the target at a wavelength band determined, at least in part, by the characteristics of the particular radiation source or sources active at the time and of filter 114. System 100 generates a digital representation of the target by digitizing the signals generated by the array of detection elements at a given time. By combining representations generated in response to irradiation of the target by different electromagnetic radiation sources, each configured to generate electromagnetic radiation in a different wavelength band or bands, with the characteristics of the radiation sources, and the characteristics of the filter, system 100 can determine reflectances with high spatial and spectral resolution.

Radiation sources 102 generate electromagnetic radiation for irradiating the target 105. At least some of the radiation generated by radiation sources 102 is reflected by the target 105 according to the material characteristics of the target 105. Radiation generated by one or more radiation sources 102 that is reflected by the target back to the imaging system 100 can pass through aperture 112 and be focused by lens 104 onto imager 106 for detection. Thus, at least some of the electromagnetic radiation detected by the detector 116 is generated by one or more of radiation sources 102. By defining the spectrum of the radiation generated by the radiation sources, the characteristics of at least some of the radiation detected at the detector 116 is known. System 100 determines reflectances of the target at multiple wavelengths, in part, by generating a series of frames, each based on irradiation of the target with electromagnetic radiation in a different wavelength band (i.e., generated by a different radiation source).

Figure 2:
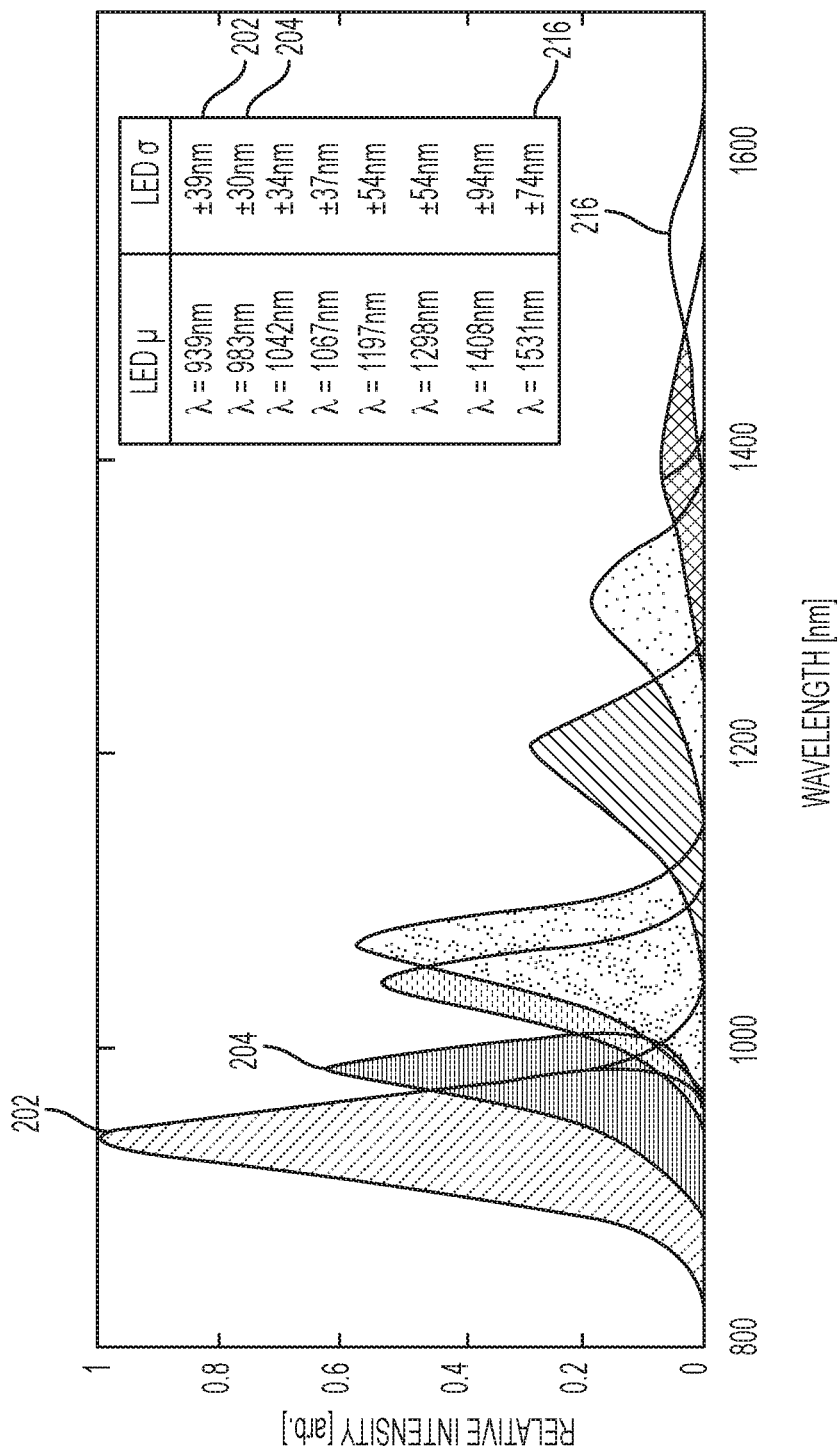
FIG. 2 is a graph illustrating the spectral response of a plurality of electromagnetic radiation sources, according to some embodiments.

Thus, each of radiation sources 102 can be configured to generate electromagnetic radiation in a different wavelength band or set of wavelength bands from the other radiation source(s) 102. For example, a first radiation source 102 may generate electromagnetic radiation in a first wavelength band and a second radiation source 102 may generate electromagnetic radiation in a second wavelength band. FIG. 2 illustrates the characteristic emittances of eight LED radiation sources according to one embodiment. Each radiation source is configured to generate electromagnetic radiation in a distinct wavelength band. For example, a first radiation source of radiation sources 102 generates radiation according to the characteristic intensity of curve 202 and a second radiation source of radiation sources 102 generates radiation according to the characteristic intensity of curve 204. The table in FIG. 2 shows the peak intensity and full width at half maximum (FWHM) bandwidths of the curves shown in the graph. As shown in the table, the radiation generated by the first radiation source (curve 202) has peak intensity at 939 nm and a FWHM bandwidth of +/−39 nm. The radiation generated by the second radiation source of radiation sources 102 as shown in curve 204 has peak intensity at 983 nm and a FWHM bandwidth of +/−30 nm.

According to some embodiments, one or more electromagnetic radiation sources 102 are configured to generate electromagnetic radiation in a narrow wavelength band. For example, radiation sources may be configured to generate radiation with a FWHM bandwidth of less than 1000 nm, less than 900 nm, less than 800 nm, less than 500 nm, less than 300 nm, less than 200 nm, less than 100 nm, less than 90 nm, less than 80 nm, less than 70 nm, less than 50 nm, less than 40 nm, less than 20 nm, less than 10 nm, or less than 1 nm. One or more radiation sources may be configured to generate radiation with a FWHM bandwidth of greater than 1 nm, greater than 10 nm, greater than 20 nm, greater than 50 nm, greater than 70 nm, greater than 100 nm, greater than 200 nm, greater than 400 nm, greater than 500 nm, or greater than 1000 nm.

In some embodiments, a radiation source includes an array of emitters, each configured to generate electromagnetic radiation in the same wavelength band. In other words, the emitters share the same characteristic spectral response. In some embodiments, a radiation source is a combination of emitters or sets of emitters, wherein each set is configured to generate a different wavelength band. Thus, a radiation source may be a combination of discrete wavelength bands. For example, a first set of emitters may be configured to generate electromagnetic radiation in a first wavelength band, a second set of emitters may be configured to generate electromagnetic radiation in a second wavelength band, and a radiation source may be a combination of the first and second sets of emitters such that the electromagnetic radiation generated by the radiation source includes radiation in the first and second wavelength bands.

Emitters for radiation sources may be selected based on the ability to generate radiation in relatively narrow wavelength bands in the electromagnetic spectrum of interest and based on the ability to be turned on and off at a high rate. According to some embodiments, the minimum time from excitation to settling (on to full off time) of one or more emitters may be less than 1 second, less than 500 milliseconds, less than 100 milliseconds, less than 50 milliseconds, less than 10 milliseconds, less than 5 milliseconds, less than 2 milliseconds, less than 1 milliseconds, or less than 500 nanoseconds. In some embodiments, emitters include light emitting diodes (LEDs), which can be chosen to generate electromagnetic radiation in narrow bands across the ultraviolet, visible, and infrared spectra, and have fast response time. In some embodiments, emitters include laser diodes. Laser diodes can be much narrower in spectral response than LEDs and, thus, more may be required to cover the full spectral range of the imager. Laser diodes may be much brighter than LEDs and are generally much more expensive. In some embodiments, one or more emitters are commercial off-the-shelf (COTS) components (e.g., LEDs sold by Roithner, Thorlabs, and Electro Optical Components). One or more emitters may be custom designed.

In some embodiments, system 100 includes radiation sources that cover the spectral range of the detector 116. For example, the detector 116 may be configured to detect electromagnetic radiation in the SWIR range and emitters of the radiation sources may be selected to emit radiation across that range. The wavelength band of one or more radiation sources may overlap the wavelength band of one or more other radiation sources. In some embodiments, radiation sources may generate distinct bands of radiation (i.e., the bands do not overlap). For example, in the embodiment shown in FIG. 2, the first and second radiation sources illustrated by curves 202 and 204, respectively, overlap whereas the first radiation source and the eighth radiation source represented by curve 216 do not overlap. In some embodiments, the wavelength of peak intensity of each radiation source may be different than the wavelength of peak intensity of every other source.

As described above, electromagnetic radiation generated by a radiation source 102 irradiates the target 105. At least some of the radiation is reflected by the target 105 based, in part, on the target's 105 reflectance characteristics. Filter 114 and detector 116 of imager 106 are positioned in the optical path and aligned such that radiation from the target passes through lens 104, through filter 114, and impinges on the focal plane of detector 116. The focal plane of detector 116 includes an array of detection elements that receive the filtered radiation and output electrical signals on an element-by-element (i.e., pixel-by-pixel) basis corresponding to the intensity of radiation received across the electromagnetic band to which the detector 116 is sensitive and within which the filter passes radiation. These signals are then converted into pixel data in a well-known manner.

Detector 116 may be implemented using any technology that creates signals from which pixel data can be created, including but not limited to photodiodes, charge coupled devices (CCD), and photocurrent sensors. In some embodiments, detector 116 is configured based on the range of wavelengths in which the imaging system is intended to operate. For example, the imaging system may be designed to generate reflectances in the visible, VNIR, and SWIR wavelength bands, and the detector may be configured to detect electromagnetic radiation in these bands. In some embodiments, a SWIR1 (950 nm-1650 nm) detector is selected to enable the detection of specific materials of interest while balancing cost. Detectors may be COTS components, for example, from supplier such as Sensors Unlimited, Raptor Photonics, FLIR, Princeton Instruments, Xenics, etc. Detectors may be made from a number of materials, including but not limited to: silicon, InGaAs, PbSe, PbS, InSb, and MCT. Detectors may be configured or selected based on various performance parameters such as sensitivity, maximum frame rate, sensing band, spatial resolution, and cost. Examples of detectors according to some embodiments are staring focal plane arrays (FPAs) in mid, large and mega pixel format, including 320×256, 640×512 and 1K×1K pixel arrays. Frame rates of detectors according to some embodiments can be any rate from low frame rates such as 1 frame per second to up to very high frame rates of up to 10,000 frames per second. A detector array may be integrated with a readout integrated circuit in order to collect the detection elements signals.

Figure 3:
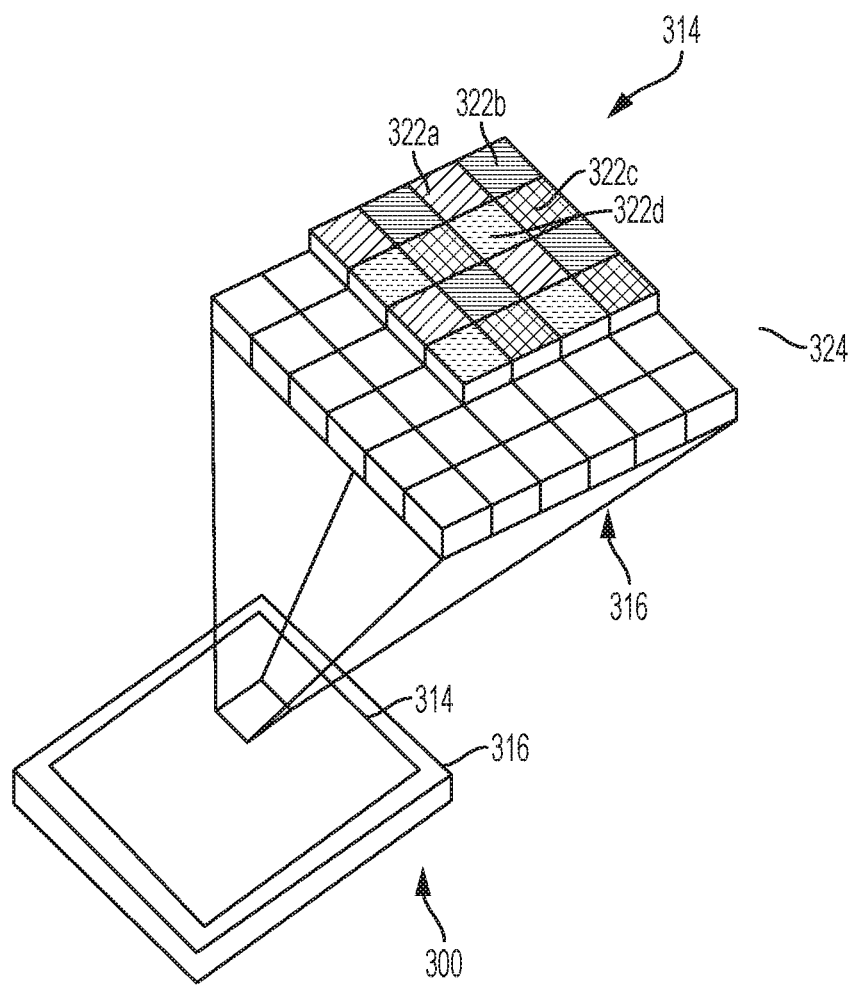
FIG. 3 illustrates a detector and filter array, according to some embodiments.

Filter 114 is positioned in front of detector 116 to filter the radiation before it impinges on detector 116. Filter 114 may include an array of filter elements. An example of the filter and detector arrangement according to one embodiment is shown in FIG. 3. Imager 300 includes filter 314 and detector 316. Filter 314, which is disposed on top of detector 316, includes an array of filter elements, a subset of which is shown in FIG. 3. In this embodiment, each filter element corresponds to a particular detection element 324 in a one-to-one fashion. In some embodiments, each filter element covers multiple detection elements. The array of filter elements may include filter elements of multiple types, each of which passes radiation in a different wavelength band or set of wavelength bands. Filter 314 of FIG. 3 includes four types of filter elements arranged in a 2×2 block. Filter element 322a is a first type, filter element 322b is a second type, filter element 322c is a third type, and filter element 322d is a fourth type. This same pattern may be repeated across the array of detection elements. Filter element 322a (and the other filter elements of the same types) is configured to pass radiation with wavelengths in a first wavelength band or set of wavelength bands, second filter element 322b is configured to pass radiation with wavelengths in a second wavelength band or set of wavelength bands, etc.

Any number of filter types in any arrangement may be used. For example, some embodiments use repeating 3×3 blocks of filter elements, each of a different type, totaling 9 filter types for filtering 9 different bands. Other arrangements may be used according to other embodiments, including other square-block patterns such as 4×4 blocks and 5×5 blocks, rectangular blocks such as 2×3 blocks and 3×5 blocks. Other patterns of filter types may be used according to other embodiments. For example, an irregular pattern may be used rather than a block pattern or more of one type of filter may be used than the other types. In some embodiments, a first filter type could pass 2, 3, 4 or more bands. Filter types do not necessarily need to pass the same number of bands each.

In some embodiments, a custom filter array arranged with a COTS or custom detector may be used. Examples of COTS detectors with built-in filter arrays may be obtained from Corning, Imec, and Pixelteq. Custom filter arrays may be built and installed in front of a custom or COTS detector by any skilled third party. Silicon sensors are widely abundant and nearly all include a Bayer pattern by default with three (red, green, blue) spectral filters built onto the focal plane.

Figure 4:
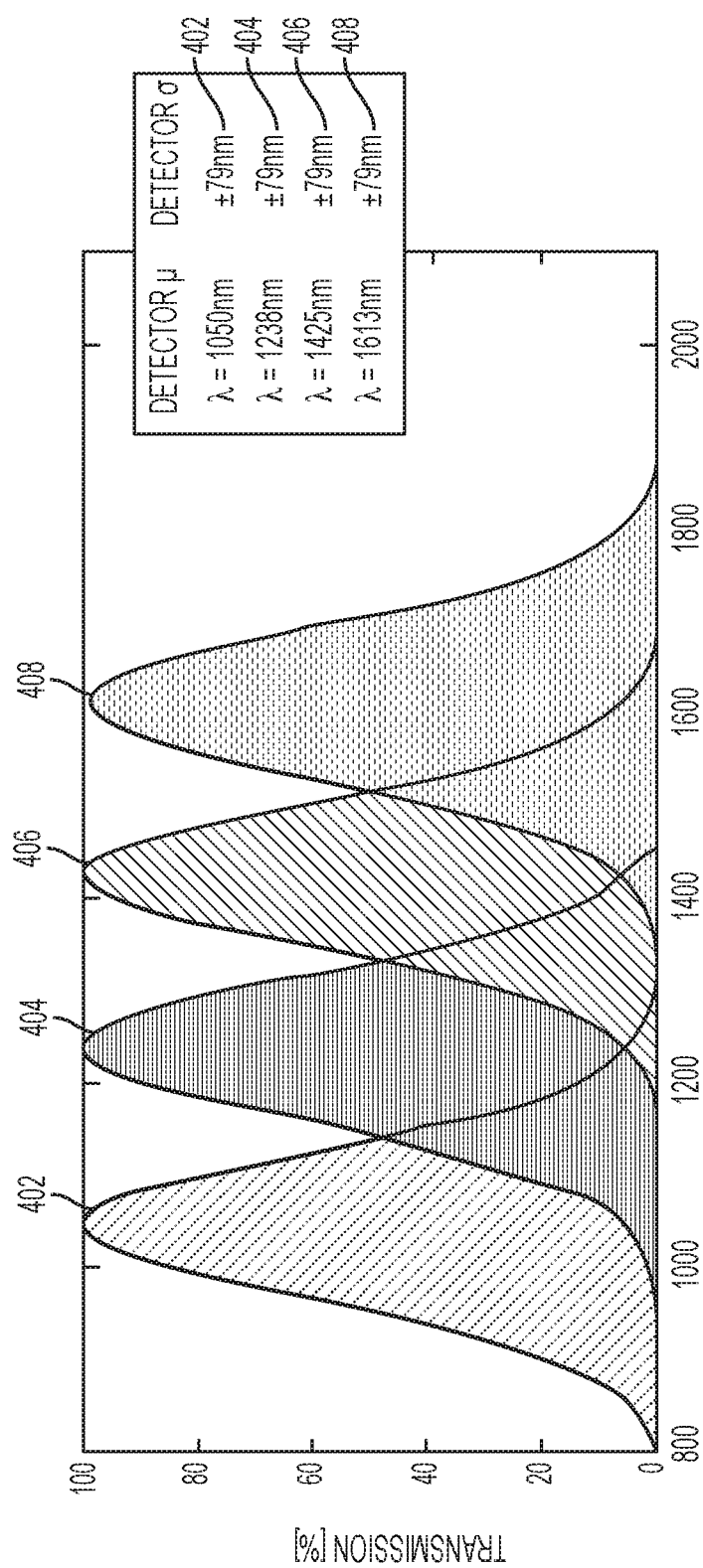
FIG. 4 is a graph illustrating the spectral response of a plurality of filter types, according to some embodiments.

FIG. 4 illustrates the transmission characteristics for four filter element types 402, 404, 406, and 408, according to some embodiments. Filter element type 402 has a transmission peak at a wavelength of approximately 1050 nm and a FWHM bandwidth of +/−79 nm. Filter element type 404 is shown to have a transmission peak at a wavelength of 1238 nm and a FWHM bandwidth of +/−79 nm. The filter element types may be configured to pass overlapping or non-overlapping bands of radiation. In some embodiments, the filter element types cover the entire spectrum detectable by the detector.

According to some embodiments, one or more filter types are configured to transmit radiation in a relatively narrow wavelength band. For example, filter types may be configured to transmit radiation with a FWHM bandwidth of less than 1000 nm, less than 900 nm, less than 800 nm, less than 500 nm, less than 300 nm, less than 200 nm, less than 100 nm, less than 90 nm, less than 80 nm, less than 70 nm, less than 50 nm, less than 40 nm, less than 20 nm, less than 10 nm, or less than 1 nm. One or more filter types may be configured to transmit radiation with a FWHM bandwidth of greater than 1 nm, greater than 10 nm, greater than 20 nm, greater than 50 nm, greater than 70 nm, greater than 100 nm, greater than 200 nm, greater than 400 nm, greater than 500 nm, or greater than 1000 nm. In some embodiments, the wavelength of peak transmission of each filter type may be different than the wavelength of peak transmission of every other filter types. In some embodiments, the transmission band of a given filter type overlaps the transmission band of one or more filter types. In some embodiments, transmission bands are discrete (non-overlapping).

The electromagnetic radiation detected by the detection element overlaid by filter element 322a in FIG. 3, for example, is based on the amount of electromagnetic radiation reflected by the corresponding portion of the target and on the wavelength band passed by filter element 322a. Similarly, the electromagnetic radiation detected by the detection element overlaid by filter element type 322b is based on the amount of electromagnetic radiation reflected by the corresponding spatial portion of the target and on the wavelength band passed by filter type 322b. Thus, the signals generated by the detection elements in response to illumination of the target by a radiation source include both spatial (in terms of the relative position of the detection elements in the array) and spectral information. Generally, increasing the numbers of filter element types can increase the number of discrete wavelength bands at which the reflectivity can be determined by the system.

Imager 106 generates a frame (digital representation) of the target based on the detected filtered electromagnetic radiation received at the detector. The generation of frames may be controlled by controller 108. Controller 108 controls activation and de-activation of radiation sources 102 along with generation (collection) of the frames. In some embodiments, the controller coordinates the generation of a frame to capture the reflected radiation after irradiation of the target with radiation from a first radiation source followed by the generation of a frame to capture the reflected radiation without irradiation of the target with any of the radiation sources 102. As discussed in more detail below, this subsequent frame can be subtracted from the first frame in order to determine the reflected radiation that is due solely to the radiation generated by the radiation source 102 activated for the first frame, as opposed to the summation of the reflected radiation from the radiation source and another source such as sun 150. Thus, controller 108 controls the fast on and off triggering of the radiation sources and the matching triggering of the imager 106. Controller 108 may include one or more components that coordinate the triggering of multiple emitters of a radiation source such that the emitters turn on and off at the same time. In some embodiments, controller 108 also controls shutter 118 in a well-known manner to control the exposure of the detector to the received electromagnetic radiation. Controller 108 can be configured for fast triggering of the radiation sources and imager. Triggering (on/off) rates according to some embodiments can be any rate from low rates such as 1 Hz to up to high rates of such as 10 kHz. Triggering rates may be greater than 1 Hz, greater than 10 Hz, greater than 100 Hz, greater than 500 Hz, greater than 1 kHz, and greater than 10 kHz.

Controller 108 may include one or more processors, microcontrollers, ASICs, DSPs, ADCs, etc., to control the triggering of the radiation sources and the capturing of frames. In some embodiments, one or more Arduinos (microcontroller boards) are used. Other options include 8-bit microcontrollers (MCUs), Atmel AVR family, TI MSP430 family, Microchip PIC family. Almost any 32-bit microcontroller can perform all functions of an 8-bit MCU (example: the ARM family of microcontrollers/processors).

The frames generated by imager 106 are processed by processing unit 110 to generate the reflectances of the target. The processing steps used by processing unit 110 to generate the reflectance data based on the collected frames are described in more detail below. Processing unit 110 may be built into a single physical unit along with the imager 106, controller 108, and radiation sources 102, or may be a standalone unit. The frames required to generate the reflectances of the target scene may be generated at one time and stored (for example in a memory in or connected to controller 108 or in a memory in or connected to processing unit 110) for later transfer to processing unit 110 for processing. In some embodiments, one or more frames are transferred to and stored by processing unit 110 during the frame capture process.

Processing unit 110 can determine reflectances for each spatial location of the target as defined by the spatial resolution (e.g., based on the pixel dimensions of the detector) of the detector 116. Reflectance values can be determined for each of multiple wavelength bands based on the frames generated by imager 106, the spectral responses of the filter types in filter 114, and the spectral responses of the electromagnetic radiation sources 102. Thus, the data cube generated by processing unit has three dimensions: two spatial dimensions and one spectral dimension. The spectral information at each pixel as generated by processing unit 110 can be used in conjunction with known characteristics of materials to identify different materials present in the target.

In some embodiments, electromagnetic radiation sources 102, aperture 112, filter 114, and detector 116 of system 100 are fixed with respect to one another. In contrast to some conventional imagers in which one or more aperture, detector, filter, etc. move relative to one another in order to expose the detector to a different portion of the scene (e.g., movable aperture or moveable lens) or to expose the detector to a different portion of a spectrum (e.g., movable detector or moveable filter), the fixed positioning of these components enables systems described herein to be smaller, lighter weight, more robust, and lower cost.

Systems, according to the present disclosure, may be configured to operate in a number of regions of the electromagnetic spectrum. For example, systems may be configured to operate in a region of wavelengths of less than 0.01 nm, with x-rays in a region of wavelengths from 0.01 nm to 10 nm, with ultraviolet radiation in a region of wavelengths from 10 nm to 380 nm, with visible light in a region of wavelengths from 380 nm to 700 nm, with infrared radiation in a region of wavelengths from 700 nm to 1 mm, etc. Some embodiments operate across more than one of these regions. Some embodiments operate across portions of one or more of these regions. For example, embodiment may operate in the NIR region at wavelengths ranging from 750 nm to 950 nm, in the SWIR region from 950 nm to 2500 nm, in the mid-wavelength infrared (MWIR) region from 2500 nm to 8000 nm, in the long-wavelength infrared region from 8000 nm to 15000 nm, or the far infrared (FIR) region from 15000 nm to 1 million nm range. According to some embodiments, systems may be configured to operate with wavelengths of at least 10 nm, at least 380 nm, at least 700 nm, at least 1400 nm, at least 3000 nm, at least 800 nm, or at least 15000 nm. According to some embodiments, systems may be configured to operate with wavelengths of less than 15000 nm, less than 800 nm, less than 3000 nm, less than 1400 nm, less than 700 nm, less than 380 nm, or less than 10 nm.

The spatial and spectral resolution of a radiance spectrum cube generated by a system such as system 100 can be tailored to a specific application by selecting the numbers and spectral responses of the electromagnetic radiation sources, the number and spectral responses of the filter types, and the pixel density and spectral response of the detector array, based on the principles described herein. Generally, the greater the number of radiation sources, the higher the spectral resolution of the resulting spectral cube. The spectral resolution of the resulting spectral cube can also be increased by increasing the number of filter types. However, the spatial resolution of the cube may be reduced as the number of types increases because fewer spatial locations are being sampled for each filter type. A detector with higher pixel density can be used to increase the spatial resolution of the spectral cube.

Method

Figure 5A:
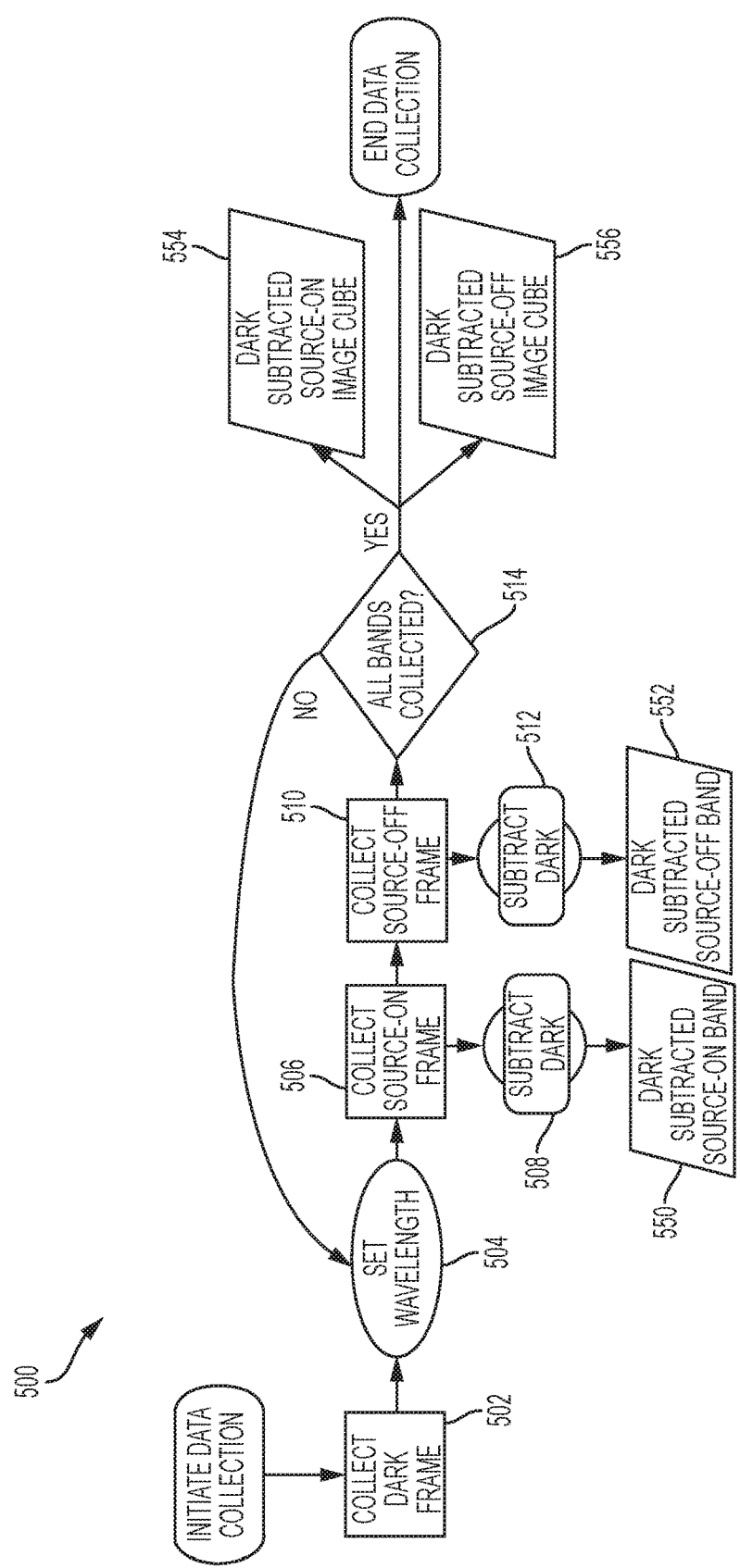
FIG. 5A is a flow diagram illustrating a frame collection process, according to some embodiments.

FIG. 5A illustrates method 500, which can be used to generate the reflectances of a target scene with high spatial and spectral resolution by capturing multiple high spatial resolution frames of the target scene while irradiating the target with electromagnetic radiation in different wavelength bands at different times. Method 500 can be performed using systems and devices according to various embodiments described herein, such as system 100. In method 500, a target is irradiated with electromagnetic radiation alternately generated by a plurality of electromagnetic radiation sources. Radiation reflected by the target is filtered through a plurality of filters and detected by a detector to generate frames representing the amount of radiation reflected by the scene. These frames may be used, in conjunction with the characteristics of the radiation sources and the characteristics of the imager, to determine multiple reflectances for each spatial point of the target represented in the frames.

The methods described below include the collection of frames which refers to the well-known method of converting signals generated by detection elements (pixels) of a detector (e.g., focal plane array) to digital data. A frame is collected by digitally sampling the signals generated by the detection elements of the detector according to well-known methods. The frame includes data that is structured to represent a two-dimensional array of pixel values corresponding to the intensity of the radiation received at each pixel (detection element). The frame may be stored in a volatile or non-volatile memory of the system for later processing.

A dark frame is collected at step 502 with the system turned on and a shutter blocking any electromagnetic radiation from being recorded by the detector. The dark frame represents the inherent signal recorded by the detector itself due to read noise and temperature. This signal can be subtracted from one or more subsequent frames captured to account for signal caused by the detector itself. Although included in the beginning of method 500, this step may be performed at any point in the data collection sequence or may be omitted altogether.

At step 504, a wavelength band or set of wavelength bands is set to select the electromagnetic radiation source to be activated for the next frame collection. By setting the electromagnetic radiation source, the subsequent frame collected can be associated with the wavelength band or set of wavelength bands generated by the radiation source selected.

At step 506, the electromagnetic radiation source set in step 504 is activated and a frame is collected. The detector signals used to generate this frame include contributions from the electromagnetic radiation source specified in step 504, any current ambient radiation conditions in the scene, and from the detector itself. The frame may be captured by opening and closing a shutter to expose the detector for a predetermined amount of time according to well-known methods. The radiation source may be activated prior to opening of the shutter and may remain active until closing of the shutter.

At step 508, the dark frame collected in step 502 can be subtracted from the frame collected at step 506 in order to remove detector contributions from the data. The data set (550) resulting from this step is a dark-subtracted frame for the electromagnetic radiation source set in step 504. This step may be performed during the frame collection process as shown in FIG. 5A or subsequent to the frame collection process.

At step 510, the electromagnetic radiation source is deactivated and a second frame is collected, which measures the signal contribution from only the current ambient radiation conditions in the scene.

At step 512, the dark frame collected in step 502 can be subtracted from the frame collected at step 510 in order to remove detector contributions from the data. The data set (552) resulting from this step is a dark-subtracted frame associated with the electromagnetic radiation source set in step 504. This step may be performed during the frame collection process as shown in FIG. 5A or subsequent to the frame collection process.

At step 514, a determination is made whether frames have been collected for each radiation source. In some embodiments, frames may collected for a subset of radiation sources rather than for all the radiation sources and the determination is made whether frames have been collected for the subset of radiation sources. If frames have not been collected for each radiation source, the method returns to step 504 to select the next radiation source.

The collection of frames for each radiation source (or each desired radiation source), results in two sets of data. A first set (554) is a set of frames representing the target with the respective radiation source activated and the dark frame subtracted. This dark-subtracted, source-on image cube includes data having three dimensions—two spatial dimensions corresponding to the number of pixels of the detector and one spectral dimension corresponding to the number of radiation sources. According to some embodiments, one frame is captured for each of eight radiation source and, thus, data set 554 includes eight frames (also referred to herein as bands). In some embodiments, multiple frames are captured for each radiation source. For example, steps 504 through 514 may be performed multiple times for each radiation source in which case data set 554 may include multiple frames for each of the radiation sources.

The second data set (556) is a set of frames representing the target with the radiation sources deactivated and the dark frame subtracted. This dark-subtracted, source-off image cube includes data having three dimensions—two spatial dimensions corresponding to the number of pixels of the detector and one spectral dimension corresponding to the number of radiation sources. According to some embodiments, one frame is captured for each of eight radiation source and, thus, data set 556 includes eight frames (also referred to herein as bands). Although the radiation conditions for each of these frames is similar (or the same) since all the radiation sources are shut off, these frames may account for spatial shift of the imaging system relative to the target during the collection process as well as for any ambient radiation differences.

Figure 5B:
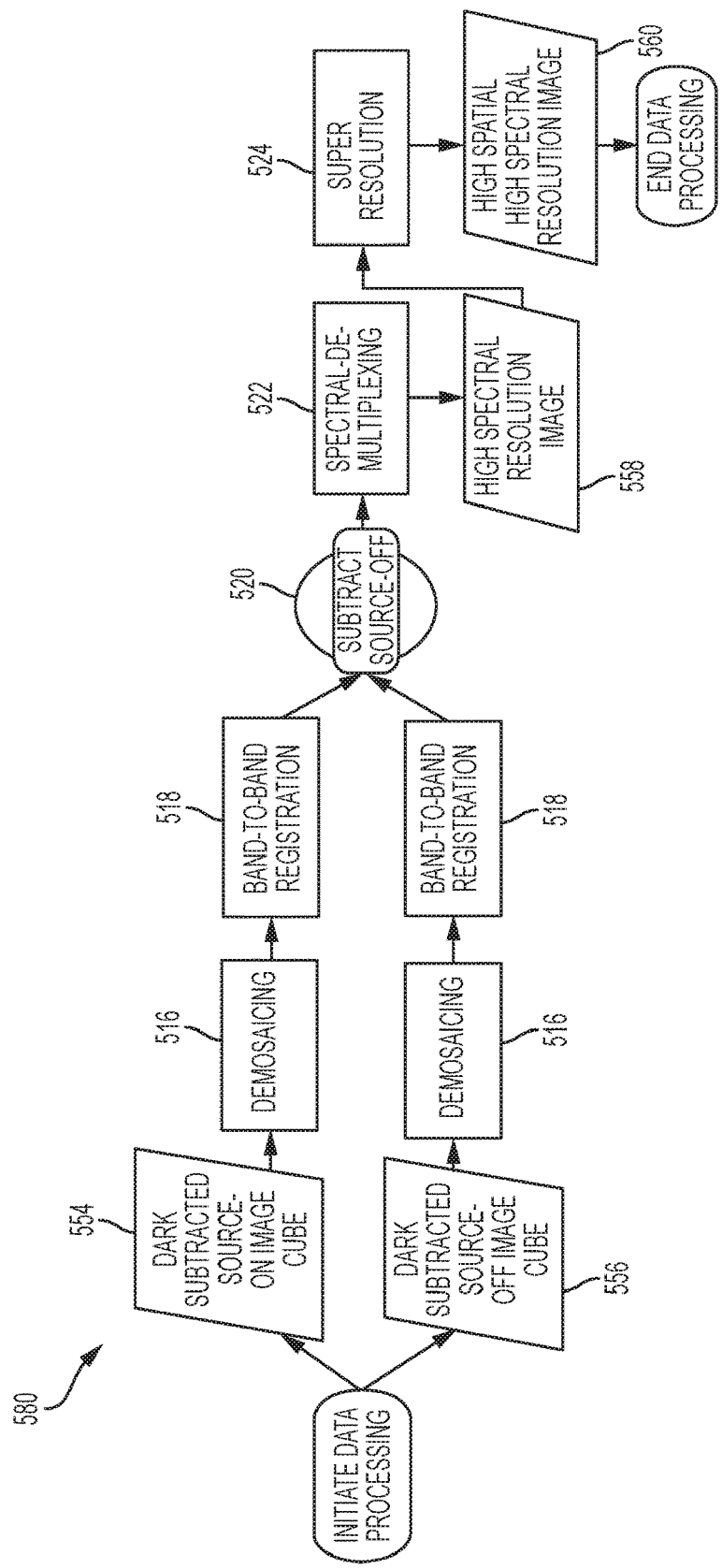
FIG. 5B is a flow diagram illustrating a process for generating a spectral cube based on the frames collected in the process of FIG. 5A, according to some embodiments.

FIG. 5B illustrates method 580, which includes the processing steps for generating reflectances of the target based on the frames collected in steps 502-514. Steps 516-524 may be performed by a component of a system that is separate from the component used to generate the frames, such as processing unit 110 of system 100. In some embodiments, steps 516-524 may be performed by a single integrated hyperspectral imaging device that also generates the frames according to steps 502-514.

In some embodiments, steps 516 and 518 are performed separately on each of data sets 554 and 556. Thus, the following description applies equally to the two data sets (image cubes). At step 516, demosaicing is applied to the dark subtracted, radiation source-on image cube of data set 554. The process of demosaicing reconstructs a full spatial resolution frame for every detection element in every frame resulting from the data collection process. For example, frames may be collected (one for each of eight radiation sources) with an imager having a filter array that includes multiple filter types. For a given frame, the portion of the data generated by the detection elements associated with a given filter type is not full resolution because it lacks the information collected by the detection elements associated with the other filter types. The demosaicing process generates a full resolution frame for each filter type by interpolating from the information contained in the detection elements associated with the other filter types and with the information contained in neighboring detection elements. Thus, a full resolution frame is generated for each filter type for each captured radiation source-on frame. For example, for an imager having four filter types, each radiation source-on frame can be converted into four full-resolution (i.e., a data point for every detection element) radiation source-on frames by the demosaicing process.

The result of the demosaicing process can be an image cube where the number of bands equals the number of filter types times the number of frames collected. For a system using eight radiation sources with a four-filter imager, the results of the demosaicing process may be an image cube with 32 full resolution frames. While this image cube can have many bands, there may be redundancy between the bands due to overlapping spectral responses of multiple filters and multiple radiation sources. Thus, the demosaiced image cube may still be considered a multispectral image cube, not a hyperspectral image cube. Examples of demosaicing algorithms, according to some embodiments, include bilinear interpolation, spline interpolation, and adaptive homogeneity directed interpolation.

At step 518, the bands generated in the demosaicing process are spatially registered to one another. Band-to-band registration is the process of aligning every demosaiced frame to the same internal coordinate system. Band-to-band registration may be performed using a mutual information (MI) based approach such as described in Dame, Amaury, "A unified direct approach for visual servoing and visual tracking using mutual information," Diss. Université Rennes 1, 2010; and Dame, Amaury, and Eric Marchand, "Second-order optimization of mutual information for real-time image registration," Image Processing, IEEE Transactions on 21.9 (2012): 4190-4203, which are hereby incorporated by reference in their entirety. MI is a metric that measures the amount of information shared between two data sets as measured by their marginal and joint histograms. When two data sets are brought into alignment with one another the value of MI computed between them will increase. Each band is registered in sequence to a selected keyframe which serves as the template for alignment. A rigid image transformation may be computed to bring the current band into alignment with the keyframe by using a nonlinear optimization method that maximizes their MI. Efficient computation of this transformation may be achieved through the use of image pyramids and/or by only using pixels from areas with significant edge information.

In some embodiments, the registering process begins with selection of a keyframe to which the other frames are registered. A current frame is selected and the MI between the keyframe and the current frame is computed. If the MI is below a predetermined threshold, the current frame is shifted relative to the keyframe (e.g., by one or more pixels in an x and/or y direction) and the MI is calculated again. This realignment and MI calculation continues for the current frame until the MI is above the predetermined threshold. This process is repeated to register each frame to the keyframe. Other registering methods may be used without departing from the principles of the systems and methods described herein. In some embodiments, registration is not performed.

As stated above, the above processes 516 and 518 are performed on both the radiation source-on cube (data set 554) and the radiation source-off cube (data set 556). At step 520, the now demosaiced and registered radiation source-off image cube is subtracted from the demosaiced and registered radiation source-on image cube. The result of this step is an image cube where the ambient radiation contributions have been subtracted from the data so that the only contribution is from the controlled radiation sources themselves.

At step 522, a de-multiplexing algorithm is applied to compute a high resolution spectral image cube from the image cube computed in step 520. A multiplexed measurement is one where each detector responds to electromagnetic radiation of several different wavelengths or several different collections of wavelengths. Such detectors may respond to electromagnetic radiation from a single large wavelength range or from several distinct wavelength ranges. Alternatively, the response may not be uniform, i.e., the detector may be twice as sensitive to electromagnetic radiation with a wavelength of 500 nm as to electromagnetic radiation with a wavelength of 600 nm. The sensitivity pattern of a detector as a function of wavelength is referred to as the detector's spectral response.

Since each measurement in a multiplexed system such as system 100 contains a weighted sum of contributions from individual wavelengths, the spectrum cannot be recovered simply by reading off the response from the detection elements. A procedure must be employed to "translate" the measured values from the detection elements to the discrete spectral values at wavelengths of interest. This procedure can take many forms but is in all cases referred to as de-multiplexing.

The measurements taken according to the systems and methods described herein are combinations of irradiation channels and responses from spectral filters. As described above, each radiation source in the system can emit radiation within a specific band of wavelengths and each set of detection elements (with a set including the detection elements associated with a given filter type) responds to radiation within another range of wavelengths (e.g., based on the filter type associated with the set of detection elements). The pattern of electromagnetic radiation emitted by a given radiation source is modified by the reflectivity spectrum of the material that the radiation impacts. Portions of the reflected radiation are then measured by the detection element sets, each of which may have a different but relatively broad band response.

Thus, if a particular instance of a system according to an embodiment has N distinct radiation sources and M distinct detection element sets, then the system collects N times M distinct multiplexed measurements. The relationship between the spectrum of the radiation source, the reflectivity of the material being sensed, and the detector's spectral response is given by $$\text{measurement} = \int \text{LED}(\lambda) \times \text{reflectivity}(\lambda) \times \text{detector}(\lambda) d\lambda$$

where $\lambda$ refers to the wavelength in nanometers, $\text{LED}(\lambda)$ refers to the characteristics of the electromagnetic radiation sources, and $\text{detector}(\lambda)$ refers to the characteristics of the detection elements (and associated filters). The integral sign indicates that a sum across all possible values of $\lambda$ is being computed. De-multiplexing according to systems and methods herein refers to the processing required to recover the reflectivity from measurements of this form.

The particular de-multiplexing process employed to recover reflectivity according to various embodiments may be a variant of linear least squares methods. In order to employ this process, a procedure for representing reflectance spectra is used. In some embodiments, the procedure employed is called an orthogonal basis expansion. A basis can be thought of as an alphabet used to express spectra. In the same way that words can be built out of letters by concatenating them, spectra can be built from a basis by forming weighted sums of basis elements. There are many possible choices for a basis but each basis has the property that any spectra can be represented by forming a weighted sum of the individual basis elements. Expressing the reflectivity in a particular basis makes the de-multiplexing problem easier since instead of requiring the reflectivity at each specific wavelength of interest, only the coefficient associated with each basis element for that spectra need to be determined. Furthermore, spectra can generally be approximated to high accuracy by using a small number of basis elements.

By considering a specific basis, a measurement matrix can be constructed for the system. This matrix describes how the device responds to each individual element in the basis. If a particular system takes N times M measurements then this matrix can have N times M rows. The number of columns of this matrix may be defined by the number of basis elements that are being recovered from the detection element signals. Classically, if N times M measurements are collected then no more than N times M basis elements can be recovered from the signals. The maximum number of basis coefficients that can be computed in practice is a complex function of the emittance spectra of the individual electromagnetic radiation sources, the detector responses, and the specific basis employed. These factors all contribute to the condition number of the matrix. The condition number of the matrix is a measure of how amenable the matrix is to a linear least squares procedure, where the ideal number is 1 and relatively large numbers indicate more difficult de-multiplexing procedures. In general, if the signal to noise ratio of the measured signals is X then the signal to noise ratio of the recovered signal will be approximately equal to the condition number times X. So, the larger the condition number, the worse the performance of the system. The condition number generally increases as the coefficients are recovered from progressively more basis elements.

Once a system matrix has been computed using the basis elements and the radiation source characteristics and detection element characteristics (e.g., spectral responses), measurements from the system can be converted into the coefficients associated with the reflectivity basis expansion by employing some variant of the linear least squares method. The canonical version of this method will compute the coefficients that best approximate the true signals given the data.

According to some embodiments, the de-multiplexing process includes, for each pixel, computing basis coefficients using a linear least squares method based on a precomputed system matrix and the ambient subtracted data set 520. The process further includes, for each pixel, computing the full resolution spectrum from basis expansion resulting in a high resolution spectral image 558.

The result of the de-multiplexing step 522 is a high spectral resolution image 558 with continuous spectral bands in reflectance space. Depending on the number of radiation sources and filter types used, the resulting image cube may be a hyperspectral image cube that includes, for example, 10 or more reflectances at discrete spectral bands for each pixel. Generated image cubes can be used in any traditional hyperspectral detection or classification methodology to locate materials of interest within the target scene.

In some embodiments, a super resolution process is applied to the high spectral resolution image 558 at step 524. Super resolution is a process of enhancing the spatial resolution of a frame in the image cube. In some embodiments, this may be done on each spectral band by leveraging the spatial redundancy in motion from handheld collection (e.g., in systems using handheld imagers) and the spectral consistency between neighboring bands. The super resolution process can be modeled as the reconstruction of a latent image whose measurements have been degraded by a blur kernel and additive noise. First, a blur kernel is estimated independently for each band, for example, as described in Xu, Li, and Jiaya Jia, "Two-phase kernel estimation for robust motion deblurring," Computer Vision—ECCV 2010, Springer Berlin Heidelberg, 2010, which is incorporated herein by reference in its entirety. A filter is used to reconstruct significant step edges, followed by the selection of important edges based on gradient magnitudes. These edges from the original and shocked images are used as input to an objective function with Gaussian regularization whose minimizer represents the desired blur kernel. The objective function has a closed form solution that can be efficiently computed in the Fourier domain. This blur kernel is then used to recover a coarse latent image estimate. This process is repeated for several iterations.

Once the blur kernels have been estimated for each band, they are used to jointly compute the deblurred images across all bands. This is done via a constrained deconvolution algorithm with Gaussian regularization to preserve smoothness across both spatial and spectral dimensions, for example, as described in Henrot, Simon, Charles Soussen, and David Brie, "Fast positive deconvolution of hyperspectral images," IEEE Transactions on Image Processing 22.2, 2013, which is incorporated herein by reference in its entirety. As before, the solution can be efficiently computed in the Fourier domain.

The result of the super resolution step 524 can be a high spatial, high spectral resolution image in reflectance space (560). The advantage of this output over the image generated in step 522 is increased spatial resolution.

The methods described above can generate hyperspectral image cubes with reflectance values for multiple discrete wavelength bands that are continuous over the spectral range of interest. In some embodiments, the number of discrete wavelength bands over the visible, NIR, and SWIR range is greater than 5, greater than 10, greater than 50, greater than 80, greater than 100, greater than 500, or greater than 1000. According to some embodiments, a hyperspectral cube of at least 50 discrete bands spanning the visible, NIR, and SWIR region can be generated using less than 10 radiation sources and less than 10 filter types. According to some embodiments, a hyperspectral cube of at least 50 discrete bands (preferably at least 80 spectral bands) spanning the SWIR region can be generated using less than 10 radiation sources and less than 10 filter types. According to some embodiments, a hyperspectral cube of at least 50 discrete bands spanning the SWIR region can be generated using less than 8 radiation sources and less than 5 filter types.

The spectral dimension of the generated hyperspectral cube may be dependent on the number of distinct radiation sources and the number of distinct filter types. According to some embodiments, N radiation sources and M filter types can enable generation of a set of M×N reflectance values, each value corresponding to the reflectance of a portion of the target at a discrete wavelength band. According to some embodiments, the number of values in the set is a fractional percentage of M×N. For example, the number of values may be at least 10% of M×N, at least 20% of M×N, at least 40% of M×N, at least 50% of M×N, at least 75% of M×N, at least 80% of M×N, at least 85% of M×N, or at least 90% of M×N.

Devices

The components described above with respect to system 100 (or a subset of the components) may be embodied in a single hyperspectral imaging device. In some embodiments, the components required to collect frames and to process the frames to generate a spectral cube, according to the systems and methods described above, may be housed within a single housing of an imaging device. In some embodiments, the device is small and portable. For example, the device may be small and light enough to be carried by two hands, by a single hand, or carried in a pocket. In some embodiments, the device is approximately the size of a shoulder-mounted video camera. In some embodiments, the device is approximately the size of a point-and-shoot camera. In some embodiments, the device weighs less than 20 pounds, less than 10 pounds, less than 5 pounds, less than 2 pounds, or less than 1 pound.

According to some embodiments, a device may be configured to collect frames for generating a spectral cube for a target that is within a given distance range from the device. For example, the distance from the device to the target may be at least 1 inch, at least 2 inches, at least 6 inches, at least 12 inches, at least 2 feet, at least 6 feet, at least 10 feet, at least 20 feet, at least 50 feet, or at least 100 feet. The distance from the device to the target may be less than 300 feet, less than 100 feet, less than 50 feet, less than 20 feet, less than 10 feet, less than 6 feet, less than 12 inches, or less than 6 inches. In some embodiments, the range may be adjusted, for example, by adjusting the configuration of the lens.

A device according to one embodiment is illustrated in the exploded view of FIG. 6A and collapsed view of FIG. 6B. Device 600 can collect the frames used to generate a hyperspectral cube of a target scene according to the systems and methods described above. Device 600 includes a plurality of electromagnetic radiation sources 602, control boards 604 and 606, lens 608, and imager 610.

The plurality of electromagnetic radiation sources 602 includes nine clusters of three emitter arrays. Each emitter array 620 includes an array of LED emitters that are all configured to generate electromagnetic radiation in the same wavelength band. In some embodiments, the emitter array is a TO-66 form factor LED array with 60 small LEDs under a resin dome. Each LED array is integrated with a heat sink for drawing the heat away from the array and to a heat sink disc.

There are nine electromagnetic radiation sources in device 600. Each radiation source includes emitter arrays from three clusters distributed about the axis of the device. For example, a first electromagnetic radiation source includes emitter arrays 622a, 622b, and 622c from three clusters. Thus, each cluster includes emitter arrays for each of three electromagnetic radiation sources.

Control board 604 is configured with one or more microcontrollers and associated circuitry to fire any combination of the nine electromagnetic radiation sources when triggered by the controller (not shown). Control board 606 includes circuitry for connecting common LED arrays so that the arrays for a given radiation source fire at the same time.

Lens 608 focuses received electromagnetic radiation on imager 610. Imager 610 includes focal plane array detector with a patterned filter array layer to filter the focused electromagnetic radiation.

Figure 7B:
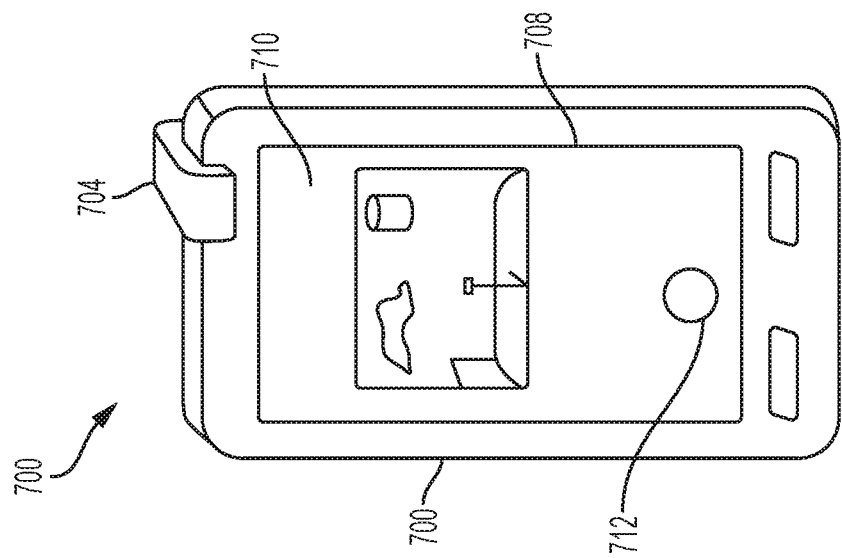
FIG. 7B is a view of the hyperspectral imaging device of FIG. 7A showing the display.
Figure 7A:
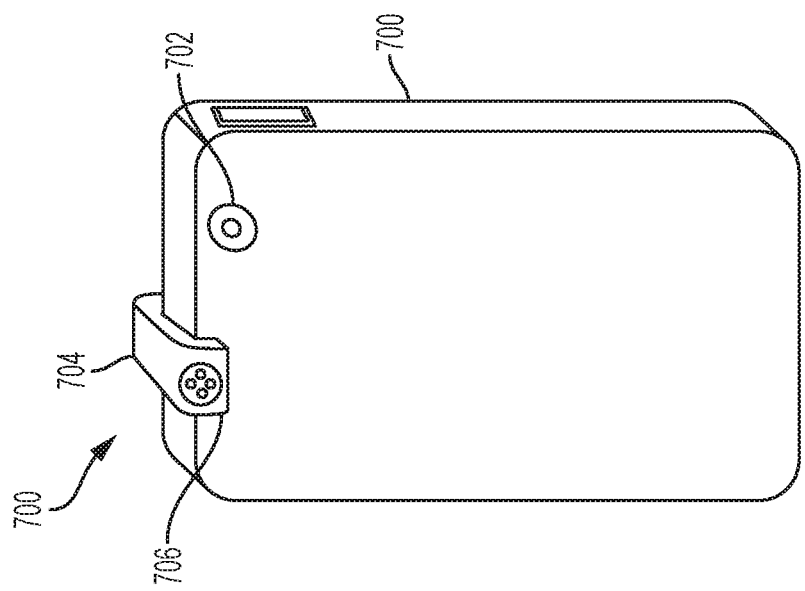
FIG. 7A is a view of a hyperspectral imaging device based on a smartphone platform showing the light sources and camera, according to one embodiment.

In some embodiments, the components of an imaging system according to the present disclosure are incorporated in a handheld electronic device such as a smartphone, PDA, tablet, etc. FIGS. 7A and 7B illustrate device 700 for generating the radiance spectrum of a target scene according to the present disclosure. Device 700 includes camera 702, flash 704, and display 708. Device 700 may be built from a COTS smartphone using the OEM camera, display, processors, memory, etc. Flash 704 may be a customized unit that includes multiple narrow-band radiation sources 706 to replace or augment the single broad-band flash of conventional smartphones. In some embodiments, camera 702 is a custom camera designed to operate in the radiation wavelength range of interest rather than in the visible spectrum of a standard smartphone camera. Each radiation source 706 produces radiation in a predefined band in accordance with the systems and methods described above. In some embodiments, flash 704 is connected to an existing port of the smartphone platform of device 700, and in other embodiments, the smartphone is customized to hardwire the flash into the control circuitry of the smartphone. Device 700 can be directed to a target scene while an imaging app is launched. A user can instruct the app to begin the data collection process. The radiation sources 706 may then be sequentially activated and deactivated according to the methods described herein and the camera can collect multiple frames. The app can then process the collected data according to the methods described above to determine the reflectance spectrum of the scene. Results of the data processing can be displayed on the screen of the smartphone.

In some embodiments, the field of view of camera 702 can be shown on display 708 to aid the user in directing camera 702 at the target. Device 700 can include one or more controls, such as soft key 712, for executing the frame collection and data processing and/or for adjusting source intensity, zoom, focus, etc. In some embodiments, device 700 may associate a set of collected frames with a single frame for display to enable the user to easily determine the relevance of the given data set. For example, a user can scroll through a collection of thumbnail images of single frames associated with multiple data sets collected for different target scenes. In some embodiments, device 700 enables a user to name a set of collected frames and/or a spectral cube generated from a set of collected frames.

Figure 8:
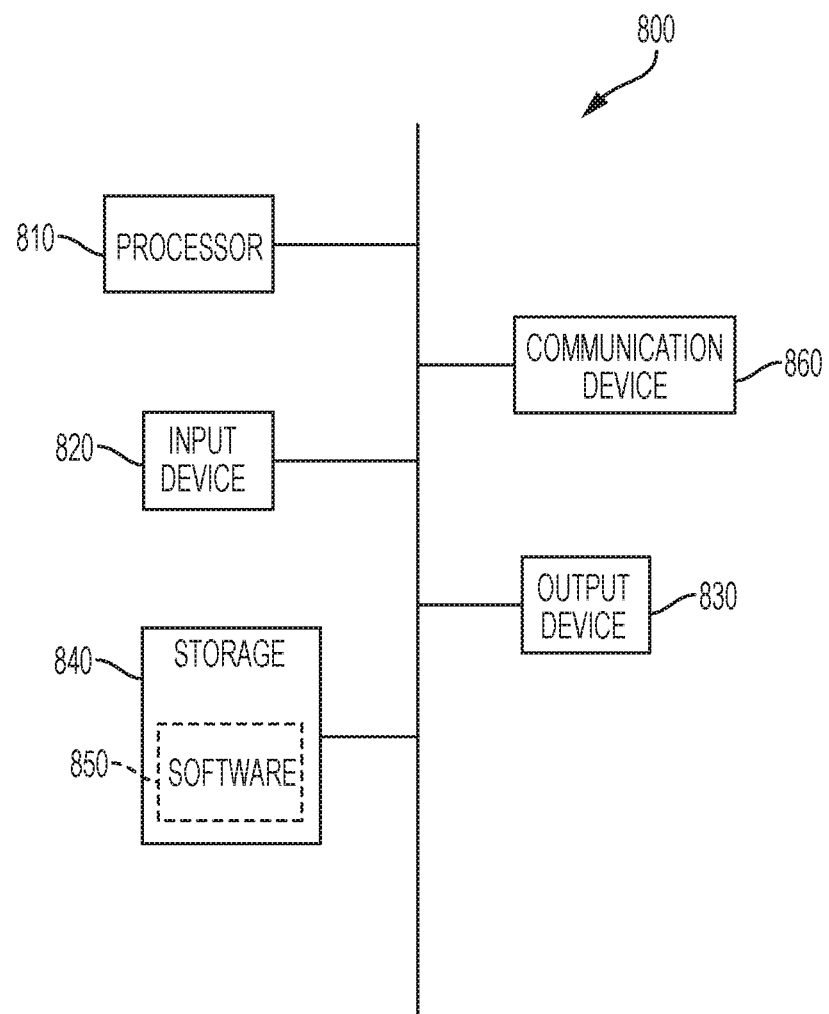
FIG. 8 is functional block diagram of a computing device according to some embodiments.

FIG. 8 illustrates an example of a computing device in accordance with some embodiments (for example, devices 600 and 700, or a computing device for implementing the functions of processing unit 110 of FIG. 1). Device 800 can be a host computer connected to a network. Device 800 can be a client computer or a server. As shown in FIG. 8, device 800 can be any suitable type of microprocessor-based device, such as a personal computer, workstation, server, or handheld computing device (portable electronic device) such as a phone or tablet. The device can include, for example, one or more of processor 810, input device 820, output device 830, storage 840, and communication device 860. Input device 820 and output device 830 can generally correspond to those described above and can either be connectable or integrated with the computer.

Input device 820 can be any suitable device that provides input, such as a touch screen, keyboard or keypad, mouse, or voice-recognition device. Output device 830 can be any suitable device that provides output, such as a touch screen, haptics device, or speaker.

Storage 840 can be any suitable device that provides storage, such as an electrical, magnetic, or optical memory including a RAM, cache, hard drive, or removable storage disk. Communication device 860 can include any suitable device capable of transmitting and receiving signals over a network, such as a network interface chip or device. The components of the computer can be connected in any suitable manner, such as via a physical bus or wirelessly.

Software 850, which can be stored in storage 840 and executed by processor 810, can include, for example, the programming that embodies the functionality of the present disclosure (e.g., as embodied in the devices as described above).

Software 850 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 840, that can contain or store programming for use by or in connection with an instruction execution system, apparatus, or device.

Software 850 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic, or infrared wired or wireless propagation medium.

Device 800 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 800 can implement any operating system suitable for operating on the network. Software 850 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated by reference.

What is claimed as new and desired to be protected by Letters Patent of the United States is:

1. A system for generating reflectance values for a target comprising:
   a plurality of electromagnetic radiation sources for irradiating the target, each electromagnetic radiation source being configured to generate radiation of a different wavelength band;
   an imager for generating a plurality of digital representations of the target comprising:
      an array of filter elements for filtering electromagnetic radiation reflected by the target through an array of filter elements; and
      a detector for detecting the filtered electromagnetic radiation at an array of detection elements;
   one or more processors;
   memory; and
   one or more programs, wherein the one or more programs are stored in the memory and configured to be executed by the one or more processors, the one or more programs including instructions for:
      sequentially activating and deactivating each electromagnetic radiation source of the plurality of electromagnetic radiation sources;
      generating a first set of digital representations of the target comprising a digital representation generated during each sequential activation;
      generating a second set of digital representations of the target comprising digital representations generated between sequential activations while the electromagnetic radiation sources are deactivated; and
      determining a set of reflectance values for each detection element of the array of detection elements, wherein each set of reflectance values comprises reflectances of the target at multiple discrete wavelength bands and each reflectance value is determined based on the first set of digital representations and the second set of digital representations.

2. The system of claim 1, wherein a first electromagnetic radiation source is configured to generate radiation of a first wavelength band, a second electromagnetic radiation source is configured to generate radiation of a second wavelength band, and the first wavelength band overlaps the second wavelength band.

3. The system of claim 1, wherein a first electromagnetic radiation source is configured to generate radiation of a first wavelength band, a second electromagnetic radiation source is configured to generate radiation of a second wavelength band, and the first wavelength band does not overlap the second wavelength band.

4. The system of claim 1, wherein the array of filter elements comprises filter elements of a first type for passing electromagnetic radiation in a first filtering wavelength band and filter elements of a second type for passing electromagnetic radiation in a second filtering wavelength band.

5. The system of claim 4, wherein the filter elements of the first type are interspersed with the filter elements of the second type.

6. The system of claim 4, wherein the first filtering wavelength band and the second filtering wavelength band are each different from wavelength bands of radiation generating by the electromagnetic radiation sources.

7. The system of claim 4, wherein the first filtering wavelength band overlaps one or more of the second filtering wavelength band and at least one wavelength band of radiation generating by the electromagnetic radiation sources.

8. The system of claim 1, wherein each filter element in the array of filter elements corresponds to a detection element in the array of detection elements.

9. The system of claim 1, wherein radiation reflected by the target passes through an aperture prior to reaching the array of filter elements and the aperture is fixed relative to the array of filter elements.

10. The system of claim 1, wherein at least one electromagnetic radiation source comprises an array of light emitting diodes or an array of laser diodes.

11. The system of claim 1, wherein each digital representation in the set of digital representations comprises an array of intensity values, each intensity value corresponding to an intensity of total electromagnetic radiation detected at the respective detection element of the array of detection elements, and the total electromagnetic radiation includes electromagnetic radiation from sources other than the plurality of electromagnetic radiation sources.

12. The system of claim 1, wherein the filter array comprises M filter types, the one or more programs include instructions for determining a set of M×N reflectance values for a portion of the target based on N digital representations of the target, each digital representation generated based on irradiation of the target by a respective one of N electromagnetic radiation sources, and each reflectance value in the set of reflectance values corresponds to the reflectance of the portion of the target at a discrete wavelength band.

13. A method for generating reflectance values for a target comprising:
sequentially activating and deactivating each electromagnetic radiation source of a plurality of electromagnetic radiation sources, each electromagnetic radiation source being configured to generate radiation of a different wavelength band, such that the target is irradiated with radiation of a different wavelength band during each sequential activation;

filtering electromagnetic radiation reflected by the target through an array of filter elements;
detecting the filtered electromagnetic radiation reflected by the target at an array of detection elements;
generating a first set of digital representations of the target based on the detected filtered electromagnetic radiation, wherein the first set of digital representations comprises a digital representation generated during each sequential activation;
generating a second set of digital representations of the target based on the detected filtered electromagnetic radiation, wherein the second set of digital representations comprises digital representations generated between sequential activations while the electromagnetic radiation sources are deactivated; and
determining a set of reflectance values for each detection element of the array of detection elements, wherein each set of reflectance values comprises reflectances of the target at multiple discrete wavelength bands and each reflectance value is determined based on the first set of digital representations and the second set of digital representations.

14. The method of claim 13, wherein a first electromagnetic radiation source is configured to generate radiation of a first wavelength band, a second electromagnetic radiation source is configured to generate radiation of a second wavelength band, and the first wavelength band overlaps the second wavelength band.

15. The method of claim 13, wherein a first electromagnetic radiation source is configured to generate radiation of a first wavelength band, a second electromagnetic radiation source is configured to generate radiation of a second wavelength band, and the first wavelength band does not overlap the second wavelength band.

16. The method of claim 13, wherein the array of filter elements comprises filter elements of a first type for passing electromagnetic radiation in a first filtering wavelength band and filter elements of a second type for passing electromagnetic radiation in a second filtering wavelength band.

17. The method of claim 16, wherein the filter elements of the first type are interspersed with the filter elements of the second type.

18. The method of claim 16, wherein the first filtering wavelength band and the second filtering wavelength band are each different from wavelength bands of radiation generating by the electromagnetic radiation sources.

19. The method of claim 16, wherein the first filtering wavelength band overlaps one or more of the second filtering wavelength band and at least one wavelength band of radiation generating by the electromagnetic radiation sources.

20. The method of claim 13, wherein each filter element in the array of filter elements corresponds to a detection element in the array of detection elements.

21. The method of claim 13, wherein radiation reflected by the target passes through an aperture prior to reaching the array of filter elements and the aperture is fixed relative to the array of filter elements.

22. The method of claim 13, wherein at least one electromagnetic radiation source comprises an array of light emitting diodes or an array of laser diodes.

23. The method of claim 13, wherein each digital representation in the set of digital representations comprises an array of intensity values, each intensity value corresponding to an intensity of total electromagnetic radiation detected at the respective detection element of the array of detection elements, and the total electromagnetic radiation includes electromagnetic radiation from sources other than the plurality of electromagnetic radiation sources.

24. The method of claim 13, wherein the filter array comprises M filter types and the first set of digital representations comprises N digital representations of the target, each digital representation generated based on irradiation of the target by a respective one of N electromagnetic radiation sources, and the method comprises determining a set of M×N reflectance values for a portion of the target based on the N digital images, wherein each reflectance value in the set of reflectance values corresponds to the reflectance of the portion of the target at a discrete wavelength band.

25. A handheld electronic device for collecting digital representations of a target comprising:
  a plurality of electromagnetic radiation sources for irradiating the target, each electromagnetic radiation source being configured to generate radiation of a different wavelength band;
  an imager for generating a plurality of digital representations of the target, the imager comprising:
    an array of filter elements for filtering electromagnetic radiation reflected by the target through an array of filter elements; and
    a detector for detecting the filtered electromagnetic radiation at an array of detection elements;
  one or more processors;
  memory; and
  one or more programs, wherein the one or more programs are stored in the memory and configured to be executed by the one or more processors, the one or more programs including instructions for:
    sequentially activating and deactivating each electromagnetic radiation source of the plurality of electromagnetic radiation sources;
    generating a first set of digital representations of the target comprising a digital representation generated during each sequential activation;
    generating a second set of digital representations of the target comprising digital representations generated between sequential activations while the electromagnetic radiation sources are deactivated; and
    determining a set of reflectance values for each detection element of the array of detection elements, wherein each set of reflectance values comprises reflectances of the target at multiple discrete wavelength bands and each reflectance value is determined based on the first set of digital representations and the second set of digital representations.

26. The device of claim 25, wherein a first electromagnetic radiation source is configured to generate radiation of a first wavelength band, a second electromagnetic radiation source is configured to generate radiation of a second wavelength band, and the first wavelength band overlaps the second wavelength band.

27. The device of claim 25, wherein a first electromagnetic radiation source is configured to generate radiation of a first wavelength band, a second electromagnetic radiation source is configured to generate radiation of a second wavelength band, and the first wavelength band does not overlap the second wavelength band.

28. The device of claim 25, wherein the array of filter elements comprises filter elements of a first type for passing electromagnetic radiation in a first filtering wavelength band and filter elements of a second type for passing electromagnetic radiation in a second filtering wavelength band.

29. The device of claim 28, wherein the filter elements of the first type are interspersed with the filter elements of the second type.

30. The device of claim 28, wherein the first filtering wavelength band and the second filtering wavelength band are each different from wavelength bands of radiation generating by the electromagnetic radiation sources.

31. The device of claim 28, wherein the first filtering wavelength band overlaps one or more of the second filtering wavelength band and at least one wavelength band of radiation generating by the electromagnetic radiation sources.

32. The device of claim 25, wherein each filter element in the array of filter elements corresponds to a detection element in the array of detection elements.

33. The device of claim 25, wherein radiation reflected by the target passes through an aperture prior to reaching the array of filter elements and the aperture is fixed relative to the array of filter elements.

34. The device of claim 25, wherein at least one electromagnetic radiation source comprises an array of light emitting diodes or an array of laser diodes.

35. The device of claim 25, wherein each digital representation in the set of digital representations comprises an array of intensity values, each intensity value corresponding to an intensity of total electromagnetic radiation detected at the respective detection element of the array of detection elements, and the total electromagnetic radiation includes electromagnetic radiation from sources other than the plurality of electromagnetic radiation sources.

36. The device of claim 25, wherein the filter array comprises M filter types and the first set of digital representations comprises N digital representations of the target, each digital representation generated based on irradiation of the target by a respective one of N electromagnetic radiation sources and the one or more programs include instructions for determining a set of M×N reflectance values for a portion of the target based on the N digital images, wherein each reflectance value in the set of reflectance values corresponds to the reflectance of the portion of the target at a discrete wavelength band.

* * * * *